US009242236B2

United States Patent
Xie et al.

(10) Patent No.: US 9,242,236 B2
(45) Date of Patent: Jan. 26, 2016

(54) CATALYTIC COMPOSITION FOR PRODUCING OLEFINS BY CATALYTIC CRACKING

(75) Inventors: Zaiku Xie, Shanghai (CN); Guangwei Ma, Shanghai (CN); Weimin Yang, Shanghai (CN); Hui Yao, Shanghai (CN); Xiaqin Yang, Shanghai (CN)

(73) Assignees: China Petroleum & Chemical Corporation, Beijing (CN); Shanghai Research Institute of Petrochemical Technology Sinopec, Shanghai (CN)

( * ) Notice: Subject to any disclaimer, the term of this patent is extended or adjusted under 35 U.S.C. 154(b) by 1048 days.

(21) Appl. No.: 12/593,199

(22) PCT Filed: Apr. 3, 2008

(86) PCT No.: PCT/CN2008/000679
§ 371 (c)(1),
(2), (4) Date: Feb. 18, 2010

(87) PCT Pub. No.: WO2008/122203
PCT Pub. Date: Oct. 16, 2008

(65) Prior Publication Data
US 2010/0145127 A1 Jun. 10, 2010

(30) Foreign Application Priority Data

Apr. 4, 2007 (CN) .......................... 2007 1 0039078

(51) Int. Cl.
*C07C 4/06* (2006.01)
*B01J 29/80* (2006.01)
*C10G 11/05* (2006.01)
*B01J 29/08* (2006.01)
*B01J 29/14* (2006.01)
*B01J 29/18* (2006.01)
*B01J 29/40* (2006.01)
*B01J 29/46* (2006.01)
*B01J 29/70* (2006.01)
*B01J 29/76* (2006.01)
*B01J 37/00* (2006.01)

(52) U.S. Cl.
CPC . *B01J 29/80* (2013.01); *C07C 4/06* (2013.01); *C10G 11/05* (2013.01); *B01J 29/084* (2013.01); *B01J 29/146* (2013.01); *B01J 29/18* (2013.01); *B01J 29/185* (2013.01); *B01J 29/40* (2013.01); *B01J 29/405* (2013.01); *B01J 29/46* (2013.01); *B01J 29/70* (2013.01); *B01J 29/7007* (2013.01); *B01J 29/7049* (2013.01); *B01J 29/7057* (2013.01); *B01J 29/76* (2013.01); *B01J 29/7615* (2013.01); *B01J 37/0009* (2013.01); *B01J 2229/18* (2013.01); *B01J 2229/20* (2013.01); *B01J 2229/42* (2013.01); *C10G 2300/1044* (2013.01); *C10G 2300/4018* (2013.01); *C10G 2400/20* (2013.01)

(58) Field of Classification Search
CPC .............. C07C 4/06; B01J 29/06; B01J 29/80
USPC .......... 585/651, 650, 648, 653; 423/700, 709, 423/712, 716, 717; 502/63, 64, 67, 71, 77, 502/86
See application file for complete search history.

(56) References Cited

U.S. PATENT DOCUMENTS

| | | | |
|---|---|---|---|
| 4,946,580 A * | 8/1990 | Fajula et al. ..................... | 502/67 |
| 5,464,799 A | 11/1995 | Casci et al. | |
| 6,211,104 B1 * | 4/2001 | Shi et al. ......................... | 502/67 |
| 6,307,117 B1 | 10/2001 | Tsunoda et al. | |
| 6,455,750 B1 | 9/2002 | Steffens et al. | |
| 6,517,807 B2 * | 2/2003 | Verduijn et al. ............... | 423/709 |
| 6,548,725 B2 * | 4/2003 | Froment et al. ............... | 585/653 |
| 6,716,784 B2 * | 4/2004 | Corma Canos et al. ........ | 502/67 |
| 6,797,155 B1 | 9/2004 | Chester et al. | |
| 6,977,320 B2 * | 12/2005 | Verduijn et al. .............. | 585/475 |

FOREIGN PATENT DOCUMENTS

| | | |
|---|---|---|
| CN | 1058195 | 1/1992 |
| CN | 1274342 | 11/2000 |

(Continued)

OTHER PUBLICATIONS

International Search Report for International Application No. PCT/CN2008/000679, mailed Jul. 17, 2008.

(Continued)

*Primary Examiner* — In Suk Bullock
*Assistant Examiner* — Sharon Pregler
(74) *Attorney, Agent, or Firm* — Finnegan, Henderson, Farabow, Garrett & Dunner, LLP

(57) ABSTRACT

A catalyst composition comprising on weight basis the following components: a) 30 to 99.5% of at least one intergrowth molecular sieve; b) 0 to 20% of a rare earth element or oxides thereof; c) 0 to 10% of at least one element from Group VA of the Periodic Table or oxides thereof; d) 0 to 10% of at least one element from Group IIIA of the Periodic Table or oxides thereof; e) 0 to 20% of at least one element from Group IB or IIB of the Periodic Table or oxides thereof; f) 0 to 20% of at least one element from Group IA or IIA of the Periodic Table or oxides thereof; and g) 0 to 65% of a binder, wherein the components b), c), d), e) and f) are supported on the component a), and contents of at least two of the components b), c), d), e) and f) are larger than zero, is described. A process for preparing said catalyst composition and a process for the production of olefins via catalytic cracking by using said catalyst composition are also described.

16 Claims, No Drawings

(56) References Cited

FOREIGN PATENT DOCUMENTS

| CN | 1397493 | 2/2003 |
| CN | 1402770 | 3/2003 |
| CN | 1413244 | 4/2003 |
| CN | 1504540 | 6/2004 |

OTHER PUBLICATIONS

English language Abstract of CN 1397493.
English language Abstract of CN 1504540.

* cited by examiner

CATALYTIC COMPOSITION FOR PRODUCING OLEFINS BY CATALYTIC CRACKING

CROSS REFERENCE OF RELATED APPLICATIONS

The present application claims the benefit of the Chinese Patent Application No. 200710039078.4, filed on Apr. 4, 2007, which is incorporated herein by reference in its entirety and for all purposes.

FIELD OF THE INVENTION

The invention relates to a catalyst composition for the catalytic cracking to produce olefins, particularly to a catalyst composition for the catalytic cracking of naphtha to produce ethylene and propylene.

BACKGROUND OF THE INVENTION

Ethylene and propylene are important basic chemical feedstock. At present, ethylene and propylene are mainly produced through catalytic cracking or steam cracking of petroleum feeds. Catalytic cracking is performed at a reaction temperature of about 50 to 200° C. lower than that of steam cracking so that compared with conventional steam cracking, catalytic cracking has the following advantages: less energy consumption; reduced rate of coking on the inner well of the cracking furnace tube and thereby prolonged operating cycle and increased lifetime of furnace tube; reduced carbon dioxide emission; flexibly adjustable product composition; and increased total yield of ethylene and propylene.

U.S. Pat. No. 6,211,104 and Chinese Patent Application CN1504540A discloses a catalyst comprising 10 to 70 wt % of clay, 5 to 85 wt % of inorganic oxide, and 1 to 50 wt % of molecular sieve, which catalyst exhibits good activity for converting various conventional cracking feedstocks to light olefins, especially ethylene. The molecular sieve used is Y zeolite or ZSM molecular sieve having MFI structure with high Si/Al ratio, and the molecular sieve is impregnated with P/Al, Mg or Ca.

Chinese Patent Application CN1274342A discloses a molecular sieve catalyst having high Si/Al ratio and pore diameter of from 0.5 to 0.65 nm, and a process for producting ethylene and propylene by using said catalyst and light hydrocarbonaceous feed containing olefins.

Chinese Patent Application 00816642.0 discloses a process for the production of ethylene and propylene, wherein a hydrocarbonaceous feed containing naphtha is treated at 550-600° C. with a zeolite having pore diameters of less than 0.7 nm.

Chinese Patent Application CN1413244A discloses a process for catalytically cracking a hydrocarbon feedstock, which process comprises contacting the feedstock with a catalyst composition comprising a primary cracking component, such as zeolite Y, and a modified mesoporous aluminophosphate material.

However, there is still a need for a novel catalyst useful in the production of olefins via catalytic cracking, which catalyst has virtues of high catalytic activity, high yield of ethylene and propylene, and lower reaction temperature.

SUMMARY OF THE INVENTION

An object of the invention is to provide a catalyst composition useful in the production of olefins via catalytic cracking, comprising on weight basis the following components:

a) 30 to 99.5% of at least one intergrowth molecular sieve;
b) 0 to 20% of at least one rare earth element or oxides thereof;
c) 0 to 10% of at least one element from Group VA of the Periodic Table or oxides thereof;
d) 0 to 10% of at least one element from Group IIIA of the Periodic Table or oxides thereof;
e) 0 to 20% of at least one element from Group IB or IIB of the Periodic Table or oxides thereof;
f) 0 to 20% of at least one element from Group IA or IIA of the Periodic Table or oxides thereof; and
g) 0 to 65% of a binder,
wherein the components b), c), d), e) and f) are supported on the component a), and contents of at least two of the components b), c), d), e) and f) are larger than zero.

Another object of the invention is to provide a process for preparing the catalyst composition of the invention, comprising i) providing at least one intergrowth molecular sieve a);
ii) supporting the following modifiers or precursors thereof on the intergrowth molecular sieve a):
b) 0 to 20 wt % of at least one rare earth element or oxides thereof;
c) 0 to 10 wt % of at least one element from Group VA of the Periodic Table or oxides thereof;
d) 0 to 10 wt % of at least one element from Group IIIA of the Periodic Table or oxides thereof;
e) 0 to 20 wt % of at least one element from Group IB or IIB of the Periodic Table or oxides thereof; and
f) 0 to 20 wt % of at least one element from Group IA or IIA of the Periodic Table or oxides thereof,
to form a modifier or precursor thereof-supported intergrowth molecular sieve, wherein the contents of the modifier components b), c), d), e) and f) are based on the weight of the final catalyst composition, and wherein the contents of at least two modifier components are larger than zero;
iii) optionally, drying the modifier or precursor thereof-supported intergrowth molecular sieve obtained from step ii);
iv) calcining the optionally-dried, modifier or precursor thereof-supported intergrowth molecular sieve; and
v) optionally, combining the calcined intergrowth molecular sieve obtained from step iv) with a binder or precursor thereof, and then molding and drying the resultant mixture, to form the catalyst composition.

Still another object of the invention is to provide a process for the production of olefins via catalytic cracking, comprising the steps of i) under catalytic cracking conditions, contacting the catalyst composition according to the invention with a cracking feedstock, to give an effluent comprising ethylene and propylene; and
ii) isolating ethylene and propylene from the effluent from step i).

DETAILED DESCRIPTION OF THE PREFERRED EMBODIMENTS

In the first aspect, the invention provides a catalyst composition, comprising on weight basis the following components:

a) 30 to 99.5% of at least one intergrowth molecular sieve;
b) 0 to 20% of at least one rare earth element or oxides thereof;
c) 0 to 10% of at least one element from Group VA of the Periodic Table or oxides thereof;
d) 0 to 10% of at least one element from Group IIIA of the Periodic Table or oxides thereof;

e) 0 to 20% of at least one element from Group IB or IIB of the Periodic Table or oxides thereof;

f) 0 to 20% of at least one element from Group IA or IIA of the Periodic Table or oxides thereof; and g) 0 to 65% of a binder, wherein the components b), c), d), e) and f) are supported on the component a), and contents of at least two of the components b), c), d), e) and f) are larger than zero.

The intergrowth molecular sieves useful in the invention include those consisting of at least two of ZSM-5, mordenite, β zeolite, Y zeolite, MCM-22, analcite, MCM-49, MCM-48, MCM-56, ZSM-23 and Magadiite molecular sieve. In a preferred embodiment, the intergrowth molecular sieve is selected from the group consisting of intergrowth molecular sieves of ZSM-5 and mordenite; intergrowth molecular sieves of ZSM-5 and β zeolite; intergrowth molecular sieves of ZSM-5 and Y zeolite; intergrowth molecular sieves of ZSM-5 and MCM-22; intergrowth molecular sieves of ZSM-5 and MCM-48; intergrowth molecular sieves of ZSM-5 and MCM-49; intergrowth molecular sieves of ZSM-5 and MCM-56; intergrowth molecular sieves of ZSM-5 and ZSM-23; intergrowth molecular sieves of ZSM-5, Magadiite and β zeolite; intergrowth molecular sieves of ZSM-5, mordenite and β zeolite; intergrowth molecular sieves of ZSM-5, mordenite and Y zeolite; intergrowth molecular sieves of ZSM-5, mordenite and MCM-22; intergrowth molecular sieves of ZSM-5, β zeolite and MCM-22; intergrowth molecular sieves of ZSM-5, β zeolite and MCM-49; intergrowth molecular sieves of ZSM-5, β zeolite and MCM-22; intergrowth molecular sieves of ZSM-5, β zeolite and MCM-49; intergrowth molecular sieves of ZSM-5, ZSM-23 and MCM-49; intergrowth molecular sieves of ZSM-5, ZSM-23 and MCM-22; and mixtures thereof. In the intergrowth molecular sieves comprising ZSM-5, the content of ZSM-5 is preferably in a range of from 40 to 99.5 wt %, more preferably in a range of from 60 to 99.5 wt %, and still more preferably in a range of from 80 to 99 wt %.

The intergrowth molecular sieve used in the invention has a molar ratio of $SiO_2$ to $Al_2O_3$ preferably in a range of from 10 to 1000, more preferably from 12 to 300, and still more preferably from 12 to 100. The content of the intergrowth molecular sieve in the catalyst composition of the invention is preferably in a range of from 40 to 99 wt %.

The rare earth element contained in the catalyst composition of the invention is preferably at least one selected from La, Ce, Nd and Pr, and more preferably is at least one selected from La and Ce. The content of the rare earth element or oxides thereof in the catalyst composition of the invention is in a range of from 0 to 20 wt %, preferably from 0.1 to 20 wt %, and more preferably from 0.5 to 15 wt %.

The element from Group VA contained in the catalyst composition of the invention is preferably at least one selected from P, As, Sb and Bi, and more preferably is P. The content of the element from Group VA or oxides thereof in the catalyst composition of the invention is in a range of from 0 to 10 wt %, preferably from 0.1 to 10 wt %, and more preferably from 0.5 to 5 wt %.

The element from Group IIIA contained in the catalyst composition of the invention is preferably at least one selected from B, Ga, In and Tl. The content of the element from Group IIIA or oxides thereof in the catalyst composition of the invention is in a range of from 0 to 10 wt %, preferably from 0.01 to 10 wt %, and more preferably from 0.1 to 5 wt %. The content of the element from Group IIIA as referred to herein does not include Al element present in the framework of the intergrowth molecular sieve.

The element from Group IB contained in the catalyst composition of the invention is preferably at least one selected from Cu, Ag and Au; and the element from Group IIB contained in the catalyst composition of the invention is preferably at least one selected from Zn and Cd. The content of the element from Group IB or IIB or oxides thereof in the catalyst composition of the invention is in a range of from 0 to 20 wt %, preferably from 0.1 to 20 wt %, and more preferably from 0.5 to 15 wt %.

The element from Group IA contained in the catalyst composition of the invention is preferably at least one selected from Li, K, Rb and Cs; and the element from Group IIA contained in the catalyst composition of the invention is preferably at least one selected from Be, Mg, Ca, Sr and Ba. The content of the element from Group IA or IIA or oxides thereof in the catalyst composition of the invention is in a range of from 0 to 20 wt %, preferably from 0.1 to 20 wt %, and more preferably from 0.5 to 10 wt %.

In a preferred embodiment, the catalyst composition of the invention further comprises at least one element selected from Ti, Zr, Hf, V, Nb and Ta or oxides thereof. The content of the at least one element selected from Ti, Zr, Hf, V, Nb and Ta or oxides thereof is preferably in a range of from 0.01 to 2 wt %, and more preferably from 0.1 to 1 wt %.

The catalyst composition of the invention comprises optionally a conventional binder such as $SiO_2$, $Al_2O_3$, $TiO_2$ or a clay, for example, kaolin. The content of the binder is preferably in a range of from 0 to 65 wt %, and more preferably from 0 to 50 wt %, based on the total weight of the catalyst composition.

The catalyst composition of the invention utilizes an intergrowth molecular sieve having a stronger acidity, a multilevel pore structure, and a good selectivity to ethylene and propylene as an essential component, and comprises one or more elements that suppress dealuminization and improve hydrothermal stability of the molecular sieve, one or more transition metal elements that have high charge density and in which electron transition is easy, and/or one or more elements that have the function of suppressing coking, i.e., the component b), c), d), e) and/or as modifier(s). Therefore, the catalyst composition of the invention has characteristics of large acid density, high acid strength, stable acidic property, and good anti-coking property, and is suitable for various convertion processes of organic substance which utilize generally a molecular sieve catalyst, especially for the catalytic cracking of alkanes to produce ethylene and propylene.

In the second aspect, the invention provides a process for preparing the catalyst composition of the invention, comprising:

i) providing at least one intergrowth molecular sieve;

ii) supporting at least two of the aforesaid modifiers or precursors thereof on the intergrowth molecular sieve by a method known per se;

iii) optionally, drying the modifier or precursor thereof-supported intergrowth molecular sieve obtained from step ii);

iv) calcining the optionally-dried, modifier or precursor thereof-supported intergrowth molecular sieve; and v) optionally, combining the calcined intergrowth molecular sieve obtained from step iv) with a binder or precursor thereof, and then molding and drying the resultant mixture, to form the catalyst composition.

The intergrowth molecular sieves used in the present invention can be prepared by mixing a silicon source, an aluminum source, an optional templating agent and water, and allowing the mixture to crystallize under hydrothermal conditions and, optionally, in the presence of suitable crystal seeds. The silicon source used in the preparation of the intergrowth molecular sieves may be any silicon source known in the art as being useful in the synthesis of molecular sieves, and non-limiting examples include metasilicates, silicates and silica sol. The aluminum source used in the preparation of the intergrowth molecular sieves may be any aluminum source known in the art as being useful in the synthesis of molecular sieves, and non-limiting examples include aluminum salts, aluminates and alumina sol. Non-limiting examples of templating agent used in the preparation of the intergrowth molecular sieves include tetrapropyl ammonium bromide, tetrapropyl ammonium hydroxide, triethyl amine, n-butyl amine, tetraethyl ammonium hydroxide, ethylene diamine, ethyl amine and mixtures thereof. The crystallizing reaction mixture has a pH value of from 10 to 13.

In a specific embodiment, an intergrowth molecular sieve is synthesized as follows: a desired amount of a silicon source and a desired amount of an aluminum source are separately dissolved in distilled water to form two solutions; then the two solutions are combined and vigorously stirred; then, if desired, one or more templating agents, M, are added to the mixed solution, and the resulting mixture is stirred for about 30 min and then adjusted with an acid (for example, diluted sulphuric acid) or a base (for example, NaOH solution) to a pH value of from 10 to 13; the mixture is supplemented with distilled water to control the molar ratio of the components in the solution to $Si:Al:Na:M:H_2O=1:0.2$ to $0.002:0.1$ to $4:0$ to $2:20$ to $40$; optionally, a desired amount of suitable crystal seeds is added, to give a crystallizing reaction mixture; the crystallizing reaction mixture is placed into an autoclave and allowed to crystallize at a temperature of 120 to 180° C. for 20 to 60 hours; resulting crystals are discharged and washed with water, and then, for example, dried at 120° C. for 4 hours and calcined at 550° C. for 3 hours, to give an intergrowth molecular sieve. An intergrowth molecular sieve in hydrogen form can be prepared by exchanging the intergrowth molecular sieve with, for example, 5% aqueous solution of ammonium nitrate at 70° C. twice and then calcining at 550° C. for 3 hours, and repeating the exchanging and calcining cycle once.

In order to prepare the catalyst composition of the invention, at lease two of the modifiers b), c), d), e) and f) or precursors thereof are supported on the intergrowth molecular sieve, and the modifier or precursor thereof-supported intergrowth molecular sieve is then calcined, optionally after a drying step. The methods for supporting the modifiers or precursors thereof are well known per se by those skilled in the art. For example, the modifiers or precursors thereof can be supported on the intergrowth molecular sieve by impregnating the intergrowth molecular sieve with an aqueous solution containing compounds of corresponding modifying elements (for example, acids or salts), or by combining the intergrowth molecular sieve with an aqueous solution containing compounds of corresponding modifying elements (for example, acids or salts) and then evaporating water. The conditions for drying and calcining the modifier or precursor thereof-supported intergrowth molecular sieve are well known by those skilled in the art. Optionally, the calcined, modifier or precursor thereof-supported intergrowth molecular sieve can be mixed with a conventional binder precursor, and then the resulting mixture is molded and dried. The binder precursor may be at least one selected from $SiO_2$ sol, $Al_2O_3$ sol, $TiO_2$ sol and clays such as kaolin. The mixture containing the binder may further comprise at least one of Sesbania cannabina powder, soluble starch and active carbon as a pore-forming agent in an amount of from 0 to 10% of the total solid weight of the mixture. The method for molding the mixture containing the binder may be any of pressing into tablet, extruding and spray drying. After the molding and drying, the catalyst composition may be further subjected to a treatment for converting crystal. For example, the catalyst composition may be treated in a vapor of a templating agent (for example, ethyl amine, ethylene diamine, or butyl amine) at 150-180° C. for 40-120 hours.

In the third aspect, the invention provide a process for the production of olefins via catalytic cracking, comprising the steps of i) under catalytic cracking conditions, contacting the catalyst composition according to the invention with a cracking feedstock, to give an effluent comprising ethylene and propylene; and ii) isolating ethylene and propylene from the effluent from step i).

The process for the production of olefins via catalytic cracking according to the invention can be performed at a conventional plant for catalytic cracking to olefins and can employ conventional reaction conditions. For example, reaction temperature may be in a range of from 550 to 700° C., reaction pressure may be in a range of from 0.001 MPa to 0.5 MPa, WHSV of the feedstock may be in a range of from 0.1 to 10 $h^{-1}$, preferably, from 0.1 to 4 $h^{-1}$, and weight ratio of water to feed oil may be in a range of from 0.1:1 to 4:1. Since the catalyst compositions of the invention have higher activities, it is possible to carry out the process of the invention at a lower reaction temperature. In principle, any of the various cracking feedstocks known in the art can be used in the process of the invention. Preferably, the process of the invention utilizes naphtha as feedstock.

EXAMPLES

The following examples are given for further illustrating the invention, but do not make limitation to the invention in any way.

In the Examples, a naphtha consisting of $C_4$ to $C_{10}$ hydrocarbons from Shanghai Gaoqiao Petrochemical Corp. was used as feedback when evaluating activities of the catalyst compositions. The naphtha has the following physical properties.

| Physical properties of the naphtha feedstock | |
|---|---|
| Item | Data |
| Density (20° C.) Kg/m³ | 704.6 |
| Boiling range | |
| Initial boiling point, ° C. | 40 |
| End boiling point, ° C. | 160 |
| Saturated vapor pressure (20° C.), KPa | 50.2 |
| Alkanes, wt % | 65.18 |
| n-Alkanes in the alkanes, wt % | >32.5 |
| Cycloalkanes, wt % | 28.44 |
| olefins, wt % | 0.17 |
| Aromatics, wt % | 6.21 |

Example 1

284 g of sodium metasilicate was dissolved in 300 g of distilled water to form a solution A. 33.3 g of aluminum sulfate was dissolved in 100 g of distilled water to form a solution B. Then the solution B was slowly poured into the solution A while vigorously stirring. The mixture was stirred for 30 min, and then was adjusted with diluted sulphuric acid to pH 11.5. Then water was added so that the resultant mixture had a molar ratio of $Si:Al:H_2O=1:0.1:40$. After stirred for 30 min, the mixture was placed in an autoclave, and maintained at 180° C. for 40 h. The resulting crystals were discharged, washed with water twice, dried at 120° C. for 4 h, and calcined at 550° C. for 3 h, to give an intergrowth molecular sieve of ZSM-5 and mordenite. It was found through XRD quantitative analysis that this intergrowth molecular sieve comprised 95 wt % of ZSM-5 and 5 wt % of mordenite. The intergrowth molecular sieve exchanged with 10 times weight of 5 wt % aqueous solution of ammonium nitrate at 70° C. twice, and then was calcined at 550° C. for 3 h. The exchanging and calcining cycle was repeated once, to give an intergrowth molecular sieve of ZSM-5 and mordenite in hydrogen form, which is referred to as FH-1.

Example 2

284 g of sodium metasilicate was dissolved in 300 g of distilled water to form a solution A. 16.7 g of aluminum sulfate was dissolved in 100 g of distilled water to form a solution B. Then the solution B was slowly poured into the solution A while vigorously stirring, and then 12.2 g of ethylene diamine and 29.4 g of tetraethyl ammonium hydroxide (mixed templating agents, referred to as M) were added thereto. The mixture was stirred for 30 min, and then was adjusted with diluted sulphuric acid to pH 11. Then water was added so that the resultant mixture had a molar ratio of Si:Al:M:$H_2O$=1:0.05:0.4:40. 2.8 g of β zeolite as crystal seeds was added to the mixture. After stirred for 30 min, the mixture was placed in an autoclave, and maintained at 160° C. for 40 h. The resulting crystals were discharged, washed with water twice, dried at 120° C. for 4 h, and calcined at 550° C. for 3 h, to give an intergrowth molecular sieve of ZSM-5 and β zeolite. It was found through XRD quantitative analysis that this intergrowth molecular sieve comprised 94.6 wt % of ZSM-5 and 5.4 wt % of β zeolite. An intergrowth molecular sieve of ZSM-5 and β zeolite in hydrogen form, which is referred to as FH-2, was prepared according to the procedure as described in Example 1.

Example 3

284 g of sodium metasilicate was dissolved in 300 g of distilled water to form a solution A. 33.3 g of aluminum sulfate was dissolved in 100 g of distilled water to form a solution B. Then the solution B was slowly poured into the solution A while vigorously stirring, and then 24.4 g of ethylene diamine were added thereto. The mixture was stirred for 20 min, and then was adjusted with diluted sulphuric acid to pH 11.5. Then water was added so that the resultant mixture had a molar ratio of Si:Al:ethylene diamine:$H_2O$=1:0.1:0.4:40. 2.8 g of Y zeolite as crystal seeds was added to the mixture. After stirred for 30 min, the mixture was placed in an autoclave, and maintained at 130° C. for 40 h. The resulting crystals were discharged, washed with water twice, dried at 120° C. for 4 h, and calcined at 550° C. for 3 h, to give an intergrowth molecular sieve of ZSM-5 and Y zeolite. It was found through XRD quantitative analysis that this intergrowth molecular sieve comprised 94.5 wt % of ZSM-5 and 5.5 wt % of Y zeolite. An intergrowth molecular sieve of ZSM-5 and Y zeolite in hydrogen form, which is referred to as FH-3, was prepared according to the procedure as described in Example 1.

Example 4

284 g of sodium metasilicate was dissolved in 300 g of distilled water to form a solution A. 33.4 g of aluminum sulfate was dissolved in 100 g of distilled water to form a solution B. Then the solution B was slowly poured into the solution A while vigorously stirring, and then 29.4 g of tetraethyl ammonium hydroxide as templating agent M was added thereto. The mixture was stirred for 20 min, and then was adjusted with diluted sulphuric acid to pH 11. Then water was added so that the resultant mixture had a molar ratio of Si:Al:M:$H_2O$=1:0.1:0.2:40. 3.0 g of Y zeolite as crystal seeds was added to the mixture. After stirred for 30 min, the mixture was placed in an autoclave, and maintained at 150° C. for 40 h. The resulting crystals were discharged, washed with water twice, dried at 120° C. for 4 h, and calcined at 550° C. for 3 h, to give an intergrowth molecular sieve of β zeolite and Y zeolite. It was found through XRD quantitative analysis that this intergrowth molecular sieve comprised 46.5 wt % of β zeolite and 53.5 wt % of Y zeolite. An intergrowth molecular sieve of β zeolite and Y zeolite in hydrogen form, which is referred to as FH-4, was prepared according to the procedure as described in Example 1.

Example 5

284 g of sodium metasilicate was dissolved in 300 g of distilled water to form a solution A. 16.7 g of aluminum sulfate was dissolved in 100 g of distilled water to form a solution B. Then the solution B was slowly poured into the solution A while vigorously stirring, and then 29.4 g of tetraethyl ammonium hydroxide and 19.9 g of hexamethylene imine (mixed templating agents, referred to as M) were added thereto. The mixture was stirred for 20 min, and then was adjusted with diluted sulphuric acid to pH 11. Then water was added so that the resultant mixture had a molar ratio of Si:Al:M:$H_2O$=1:0.05:0.4:40. 3.0 g of MCM-22 as crystal seeds was added to the mixture. After stirred for 30 min, the mixture was placed in an autoclave, and maintained at 150° C. for 40 h. The resulting crystals were discharged, washed with water twice, dried at 120° C. for 4 h, and calcined at 550° C. for 3 h, to give an intergrowth molecular sieve of β zeolite, mordenite and MCM-22. It was found through XRD quantitative analysis that this intergrowth molecular sieve comprised 54.5 wt % of β zeolite, 12.8 wt % of mordenite, and 22.7 wt % of MCM-22. An intergrowth molecular sieve of β zeolite, mordenite and MCM-22 in hydrogen form, which is referred to as FH-5, was prepared according to the procedure as described in Example 1.

Example 6

284 g of sodium metasilicate was dissolved in 300 g of distilled water to form a solution A. 16.7 g of aluminum sulfate was dissolved in 100 g of distilled water to form a solution B. Then the solution B was slowly poured into the solution A while vigorously stirring, and then 12.2 g of ethylene diamine and 19.9 g of hexamethylene imine (mixed templating agents, referred to as M) were added thereto. The mixture was stirred for 20 min, and then was adjusted with diluted sulphuric acid to pH 11. Then water was added so that the resultant mixture had a molar ratio of Si:Al:M:$H_2O$=1:0.05:0.4:40. 3.0 g of MCM-22 as crystal seeds was added to the mixture. After stirred for 30 min, the mixture was placed in an autoclave, and maintained at 150° C. for 40 h. The resulting crystals were discharged, washed with water twice, dried at 120° C. for 4 h, and calcined at 550° C. for 3 h, to give an intergrowth molecular sieve of mordenite and MCM-22. It was found through XRD quantitative analysis that this intergrowth molecular sieve comprised 61.5 wt % of mordenite and 38.5 wt % of MCM-22. An intergrowth molecular sieve of mordenite and MCM-22 in hydrogen form, which is referred to as FH-6, was prepared according to the procedure as described in Example 1.

Example 7

284 g of sodium metasilicate was dissolved in 300 g of distilled water to form a solution A. 25.1 g of aluminum sulfate was dissolved in 100 g of distilled water to form a solution B. Then the solution B was slowly poured into the solution A while vigorously stirring, and then 12.2 g of ethylene diamine and 19.9 g of hexamethylene imine (mixed templating agents, referred to as M) were added thereto. The mixture was stirred for 20 min, and then was adjusted with diluted sulphuric acid to pH 11. Then water was added so that the resultant mixture had a molar ratio of Si:Al:M:$H_2O$=1:0.067:0.4:40. 3.0 g of MCM-22 as crystal seeds was added to the mixture. After stirred for 30 min, the mixture was placed in an autoclave, and maintained at 150° C. for 40 h. The resulting crystals were discharged, washed with water twice, dried at 120° C. for 4 h, and calcined at 550° C. for 3 h, to give an intergrowth molecular sieve of mordenite, MCM-22 and MCM-49. It was found through XRD quantitative analysis that this intergrowth molecular sieve comprised 22.3 wt % of MCM-49 molecular sieve, 47.9 wt % of mordenite, and 29.8 wt % of MCM-22. An intergrowth molecular sieve of mordenite, MCM-22 and MCM-49 in hydrogen form, which is referred to as FH-7, was prepared according to the procedure as described in Example 1.

Example 8

284 g of sodium metasilicate was dissolved in 300 g of distilled water to form a solution A. 33.4 g of aluminum sulfate was dissolved in 100 g of distilled water to form a solution B. Then the solution B was slowly poured into the solution A while vigorously stirring, and then 12.2 g of ethylene diamine (templating agent, referred to as M) was added thereto. The mixture was stirred for 20 min, and then was adjusted with diluted sulphuric acid to pH 11. Then water was added so that the resultant mixture had a molar ratio of Si:Al:M:$H_2O$=1:0.1:0.2:40. 3.0 g of Y zeolite as crystal seeds was added to the mixture. After stirred for 30 min, the mixture was placed in an autoclave, and maintained at 160° C. for 40 h. The resulting crystals were discharged, washed with water twice, dried at 120° C. for 4 h, and calcined at 550° C. for 3 h, to give an intergrowth molecular sieve of mordenite and Y zeolite. It was found through XRD quantitative analysis that this intergrowth molecular sieve comprised 54.5 wt % of mordenite, and 45.5 wt % of Y zeolite. An intergrowth molecular sieve of mordenite and Y zeolite in hydrogen form, which is referred to as FH-8, was prepared according to the procedure as described in Example 1.

Example 9

284 g of sodium metasilicate was dissolved in 300 g of distilled water to form a solution A. 16.7 g of aluminum sulfate was dissolved in 100 g of distilled water to form a solution B. Then the solution B was slowly poured into the solution A while vigorously stirring, and then 29.4 g of tetraethyl ammonium hydroxide and 19.9 g of hexamethylene imine (mixed templating agents, referred to as M) were added thereto. The mixture was stirred for 20 min, and then was adjusted with diluted sulphuric acid to pH 11. Then water was added so that the resultant mixture had a molar ratio of Si:Al:M:$H_2O$=1:0.05:0.4:40. 3.0 g of MCM-22 as crystal seeds was added to the mixture. After stirred for 30 min, the mixture was placed in an autoclave, and maintained at 150° C. for 40 h. The resulting crystals were discharged, washed with water twice, dried at 120° C. for 4 h, and calcined at 550° C. for 3 h, to give an intergrowth molecular sieve of ZSM-5, β zeolite and MCM-22. It was found through XRD quantitative analysis that this intergrowth molecular sieve comprised 41.5 wt % of β zeolite, 37.7 wt % of ZSM-5, and 20.8 wt % of MCM-22. An intergrowth molecular sieve of ZSM-5, β zeolite and MCM-22 in hydrogen form, which is referred to as FH-9, was prepared according to the procedure as described in Example 1.

Example 10

284 g of sodium metasilicate was dissolved in 300 g of distilled water to form a solution A. 33.4 g of aluminum sulfate was dissolved in 100 g of distilled water to form a solution B. Then the solution B was slowly poured into the solution A while vigorously stirring, and then 12.2 g of ethylene diamine and 29.4 g of tetraethyl ammonium hydroxide (mixed templating agents, referred to as M) were added thereto. The mixture was stirred for 20 min, and then was adjusted with diluted sulphuric acid to pH 11. Then water was added so that the resultant mixture had a molar ratio of Si:Al:M:$H_2O$=1:0.1:0.4:40. 3.0 g of Y zeolite as crystal seeds was added to the mixture. After stirred for 30 min, the mixture was placed in an autoclave, and maintained at 150° C. for 40 h. The resulting crystals were discharged, washed with water twice, dried at 120° C. for 4 h, and calcined at 550° C. for 3 h, to give an intergrowth molecular sieve of ZSM-5, β zeolite and Y zeolite. It was found through XRD quantitative analysis that this intergrowth molecular sieve comprised 20.5 wt % of β zeolite, 38.7 wt % of ZSM-5 and 40.8 wt % of Y zeolite. An intergrowth molecular sieve of ZSM-5, β zeolite and Y zeolite in hydrogen form, which is referred to as FH-10, was prepared according to the procedure as described in Example 1.

Example 11

33.3 g of sodium metasilicate was dissolved in 100 g of distilled water to form a solution A. 57.4 g of 40 wt % silica sol was dissolved in 100 g of distilled water to form a solution B. 0.48 g of aluminum sulfate was dissolved in 20 ml of distilled water to form a solution C. The solution A and the solution C were separately slowly poured into the solution B while vigorously stirring. Next, 2.6 g of sodium hydroxide and 14.7 g of tetraethyl ammonium hydroxide were added thereto, and then 1.2 g of β zeolite as crystal seeds was added. The mixture was stirred for 20 min, and then was adjusted with diluted sulphuric acid to pH 11. Then water was added so that the resultant mixture had a molar ratio of Si:Al:Na:$H_2O$=1:0.005:0.6:40. After stirred for 30 min, the mixture was placed in an autoclave, and maintained at 160° C. for 40 h. The resulting crystals were discharged, washed with water twice, dried at 120° C. for 4 h, and calcined at 550° C. for 3 h, to give an intergrowth molecular sieve of ZSM-5, Magadiite and β zeolite. It was found through XRD quantitative analysis that this intergrowth molecular sieve comprised 50.6 wt % of ZSM-5, 24.9 wt % of β zeolite, and 24.5 wt % of Magadiite. An intergrowth molecular sieve of ZSM-5, Magadiite and β zeolite in hydrogen form, which is referred to as FH-11, was prepared according to the procedure as described in Example 1.

Example 12

33.3 g of sodium metasilicate was dissolved in 100 g of distilled water to form a solution A. 57.4 g of 40 wt % silica sol was dissolved in 100 g of distilled water to form a solution B. 0.48 g of aluminum sulfate was dissolved in 20 ml of distilled water to form a solution C. The solution A and the solution C were separately slowly poured into the solution B while vigorously stirring. Next, 2.6 g of sodium hydroxide and 1.2 g of mordenite as crystal seeds were added thereto. The mixture was stirred for 20 min, and then was adjusted with diluted sulphuric acid to pH 11. Then water was added so that the resultant mixture had a molar ratio of Si:Al:Na:$H_2O$=1:0.001:0.6:40. After stirred for 30 min, the mixture was placed in an autoclave, and maintained at 180° C. for 40 h. The resulting crystals were discharged, washed with water twice, dried at 120° C. for 4 h, and calcined at 550° C. for 3 h, to give an intergrowth molecular sieve of ZSM-5, Magadiite and mordenite. It was found through XRD quantitative analysis that this intergrowth molecular sieve comprised 40.4 wt % of ZSM-5, 21.2 wt % of mordenite, and 38.4 wt % of Magadiite. An intergrowth molecular sieve of ZSM-5, Magadiite and mordenite in hydrogen form, which is referred to as FH-12, was prepared according to the procedure as described in Example 1.

Example 13

284 g of sodium metasilicate was dissolved in 300 g of distilled water to form a solution A. 25.1 g of aluminum sulfate was dissolved in 100 g of distilled water to form a solution B. Then the solution B was slowly poured into the solution A while vigorously stirring, and then 12.2 g of triethyl amine and 29.4 g of tetraethyl ammonium hydroxide (mixed templating agents, referred to as M) were added thereto. The mixture was stirred for 20 min, and then was adjusted with diluted sulphuric acid to pH 11.5. Then water was added so that the resultant mixture had a molar ratio of Si:Al:M:$H_2O$=1:0.067:0.4:40. 2.8 g of Y zeolite as crystal seeds was added to the mixture. After stirred for 30 min, the mixture was placed in an autoclave, and maintained at 160° C. for 40 h. The resulting crystals were discharged, washed with water twice, dried at 120° C. for 4 h, and calcined at 550° C. for 3 h, to give an intergrowth molecular sieve of mordenite, β zeolite and Y zeolite. It was found through XRD quantitative analysis that this intergrowth molecular sieve comprised 35.4 wt % of mordenite, 30.3 wt % of β zeolite, and 34.3 wt % of Y zeolite. An intergrowth molecular sieve of mordenite, β zeolite and Y zeolite in hydrogen form, which is referred to as FH-13, was prepared according to the procedure as described in Example 1.

Example 14

284 g of sodium metasilicate was dissolved in 300 g of distilled water to form a solution A. 16.7 g of aluminum sulfate was dissolved in 100 g of distilled water to form a solution B. Then the solution B was slowly poured into the solution A while vigorously stirring, and then 24.4 g of ethylene diamine and 29.4 g of tetraethyl ammonium hydroxide as templating agent M were added thereto. The mixture was stirred for 20 min, and then was adjusted with NaOH and/or diluted sulphuric acid to pH 12. Then water was added so that the resultant mixture had a molar ratio of Si:Al:M:$H_2O$:$OH^-$=1:0.05:0.4:40. After stirred for 30 min, the mixture was placed in an autoclave, and maintained at 160° C. for 40 h. The resulting crystals were discharged, washed with water twice, dried at 120° C. for 4 h, and calcined at 550° C. for 3 h, to give an intergrowth molecular sieve of mordenite, β zeolite and analcite. It was found through XRD quantitative analysis that this intergrowth molecular sieve comprised 30.2 wt % of β zeolite, 48.7 wt % of mordenite, and 21.1 wt % of analcite. An intergrowth molecular sieve of mordenite, β zeolite and analcite in hydrogen form, which is referred to as FH-14, was prepared according to the procedure as described in Example 1.

Example 15

284 g of sodium metasilicate was dissolved in 300 g of distilled water to form a solution A. 16.7 g of aluminum sulfate was dissolved in 100 g of distilled water to form a solution B. Then the solution B was slowly poured into the solution A while vigorously stirring, and then 29.4 g of tetraethyl ammonium hydroxide and 19.9 g of hexamethylene imine (mixed templating agents, referred to as M) were added thereto. The mixture was stirred for 20 min, and then was adjusted with diluted sulphuric acid to pH 11. Then water was added so that the resultant mixture had a molar ratio of Si:Al:M:$H_2O$=1:0.05:0.4:40. 3.0 g of MCM-49 as crystal seeds was added thereto. After stirred for 30 min, the mixture was placed in an autoclave, and maintained at 160° C. for 40 h. The resulting crystals were discharged, washed with water twice, dried at 120° C. for 4 h, and calcined at 550° C. for 3 h, to give an intergrowth molecular sieve of ZSM-5, β zeolite and MCM-49. It was found through XRD quantitative analysis that this intergrowth molecular sieve comprised 41.6 wt % of β zeolite, 37.9 wt % of ZSM-5, and 20.5 wt % of MCM-49. An intergrowth molecular sieve of ZSM-5, β zeolite and MCM-49 in hydrogen form, which is referred to as FH-15, was prepared according to the procedure as described in Example 1.

Example 16

284 g of sodium metasilicate was dissolved in 300 g of distilled water to form a solution A. 16.7 g of aluminum sulfate was dissolved in 100 g of distilled water to form a solution B. Then the solution B was slowly poured into the solution A while vigorously stirring, and then 29.4 g of tetraethyl ammonium hydroxide and 19.9 g of hexamethylene imine (mixed templating agents, referred to as M) were added thereto. The mixture was stirred for 20 min, and then was adjusted with diluted sulphuric acid to pH 11. Then water was added so that the resultant mixture had a molar ratio of Si:Al:M:$H_2O$=1:0.05:0.4:40. 3.0 g of MCM-56 as crystal seeds was added thereto. After stirred for 30 min, the mixture was placed in an autoclave, and maintained at 140° C. for 40 h. The resulting crystals were discharged, washed with water twice, dried at 120° C. for 4 h, and calcined at 550° C. for 3 h, to give an intergrowth molecular sieve of ZSM-5, β zeolite and MCM-56. It was found through XRD quantitative analysis that this intergrowth molecular sieve comprised 40.3 wt % of β zeolite, 38.1 wt % of ZSM-5, and 21.6 wt % of MCM-56. An intergrowth molecular sieve of ZSM-5, β zeolite and MCM-56 in hydrogen form, which is referred to as FH-16, was prepared according to the procedure as described in Example 1.

Example 17

284 g of sodium metasilicate was dissolved in 300 g of distilled water to form a solution A. 16.7 g of aluminum sulfate was dissolved in 100 g of distilled water to form a solution B. Then the solution B was slowly poured into the solution A while vigorously stirring, and then 29.4 g of tetraethyl ammonium hydroxide and 12.2 g of pyrrolidine (mixed templating agents, referred to as M) were added thereto. The mixture was stirred for 20 min, and then was adjusted with diluted sulphuric acid to pH 11. Then water was added so that the resultant mixture had a molar ratio of Si:Al:M:H$_2$O=1:0.05:0.4:40. 3.0 g of ZSM-23 as crystal seeds was added thereto. After stirred for 30 min, the mixture was placed in an autoclave, and maintained at 165° C. for 70 h. The resulting crystals were discharged, washed with water twice, dried at 120° C. for 4 h, and calcined at 550° C. for 3 h, to give an intergrowth molecular sieve of ZSM-5, β zeolite and ZSM-23. It was found through XRD quantitative analysis that this intergrowth molecular sieve comprised 28.7 wt % of β zeolite, 46.4 wt % of ZSM-5, and 24.9 wt % of ZSM-23. An intergrowth molecular sieve of ZSM-5, β zeolite and ZSM-23 in hydrogen form, which is referred to as FH-17, was prepared according to the procedure as described in Example 1.

Example 18

284 g of sodium metasilicate was dissolved in 300 g of distilled water to form a solution A. 16.7 g of aluminum sulfate was dissolved in 100 g of distilled water to form a solution B. Then the solution B was slowly poured into the solution A while vigorously stirring, and then 29.4 g of tetraethyl ammonium hydroxide and 19.9 g of hexamethylene imine (mixed templating agents, referred to as M) were added thereto. The mixture was stirred for 20 min, and then was adjusted with diluted sulphuric acid to pH 11. Then water was added so that the resultant mixture had a molar ratio of Si:Al:M:H$_2$O=1:0.05:0.4:40. 3.0 g of MCM-49 as crystal seeds was added thereto. After stirred for 30 min, the mixture was placed in an autoclave, and maintained at 160° C. for 40 h. The resulting crystals were discharged, washed with water twice, dried at 120° C. for 4 h, and calcined at 550° C. for 3 h, to give an intergrowth molecular sieve of ZSM-5, mordenite and MCM-49. It was found through XRD quantitative analysis that this intergrowth molecular sieve comprised 36.7 wt % of mordenite, 44.7 wt % of ZSM-5, and 18.6 wt % of MCM-49. An intergrowth molecular sieve of ZSM-5, mordenite and MCM-49 in hydrogen form, which is referred to as FH-18, was prepared according to the procedure as described in Example 1.

Example 19

284 g of sodium metasilicate was dissolved in 300 g of distilled water to form a solution A. 16.7 g of aluminum sulfate was dissolved in 100 g of distilled water to form a solution B. Then the solution B was slowly poured into the solution A while vigorously stirring, and then 29.4 g of tetraethyl ammonium hydroxide and 19.9 g of hexamethylene imine (mixed templating agents, referred to as M) were added thereto. The mixture was stirred for 20 min, and then was adjusted with diluted sulphuric acid to pH 11. Then water was added so that the resultant mixture had a molar ratio of Si:Al:M:H$_2$O=1:0.05:0.4:40. 3.0 g of MCM-56 as crystal seeds was added thereto. After stirred for 30 min, the mixture was placed in an autoclave, and maintained at 140° C. for 40 h. The resulting crystals were discharged, washed with water twice, dried at 120° C. for 4 h, and calcined at 550° C. for 3 h, to give an intergrowth molecular sieve of ZSM-5, mordenite and MCM-56. It was found through XRD quantitative analysis that this intergrowth molecular sieve comprised 34.5 wt % of mordenite, 48.7 wt % of ZSM-5, and 16.8 wt % of MCM-56. An intergrowth molecular sieve of ZSM-5, mordenite and MCM-56 in hydrogen form, which is referred to as FH-19, was prepared according to the procedure as described in Example 1.

Example 20

284 g of sodium metasilicate was dissolved in 300 g of distilled water to form a solution A. 16.7 g of aluminum sulfate was dissolved in 100 g of distilled water to form a solution B. Then the solution B was slowly poured into the solution A while vigorously stirring, and then 40.6 g of tetrapropyl ammonium hydroxide and 12.2 g of pyrrolidine (mixed templating agents, referred to as M) were added thereto. The mixture was stirred for 20 min, and then was adjusted with diluted sulphuric acid to pH 11. Then water was added so that the resultant mixture had a molar ratio of Si:Al:M:H$_2$O=1:0.05:0.4:40. 3.0 g of MCM-23 as crystal seeds was added thereto. After stirred for 30 min, the mixture was placed in an autoclave, and maintained at 170° C. for 70 h. The resulting crystals were discharged, washed with water twice, dried at 120° C. for 4 h, and calcined at 550° C. for 3 h, to give an intergrowth molecular sieve of ZSM-5, mordenite and MCM-23. It was found through XRD quantitative analysis that this intergrowth molecular sieve comprised 31.5 wt % of mordenite, 45.2 wt % of ZSM-5, and 23.3 wt % of ZSM-23. An intergrowth molecular sieve of ZSM-5, mordenite and MCM-23 in hydrogen form, which is referred to as FH-20, was prepared according to the procedure as described in Example 1.

Example 21

284 g of sodium metasilicate was dissolved in 300 g of distilled water to form a solution A. 16.7 g of aluminum sulfate was dissolved in 100 g of distilled water to form a solution B. Then the solution B was slowly poured into the solution A while vigorously stirring, and then 14.7 g of tetraethyl ammonium hydroxide, 7.1 g of pyrrolidine and 19.9 g of hexamethylene imine (mixed templating agents, referred to as M) were added thereto. The mixture was stirred for 20 min, and then was adjusted with diluted sulphuric acid to pH 11. Then water was added so that the resultant mixture had a molar ratio of Si:Al:M:H$_2$O=1:0.05:0.4:40. 3.0 g of MCM-22 as crystal seeds was added thereto. After stirred for 30 min, the mixture was placed in an autoclave, and maintained at 160° C. for 70 h. The resulting crystals were discharged, washed with water twice, dried at 120° C. for 4 h, and calcined at 550° C. for 3 h, to give an intergrowth molecular sieve of ZSM-5, ZSM-23 and MCM-22. It was found through XRD quantitative analysis that this intergrowth molecular sieve comprised 32.5 wt % of ZSM-23, 44.7 wt % of ZSM-5, and 22.8 wt % of MCM-22. An intergrowth molecular sieve of ZSM-5, ZSM-23 and MCM-22 in hydrogen form, which is referred to as FH-21, was prepared according to the procedure as described in Example 1.

Example 22

284 g of sodium metasilicate was dissolved in 300 g of distilled water to form a solution A. 16.7 g of aluminum sulfate was dissolved in 100 g of distilled water to form a solution B. Then the solution B was slowly poured into the solution A while vigorously stirring, and then 12.2 g of ethylene diamine and 14.2 g of pyrrolidine (mixed templating agents, referred to as M) were added thereto. The mixture was stirred for 20 min, and then was adjusted with diluted sulphuric acid to pH 11. Then water was added so that the resultant mixture had a molar ratio of Si:Al:M:H$_2$O=1:0.05:0.4:40. 3.0 g of Y zeolite as crystal seeds was added thereto. After stirred for 30 min, the mixture was placed in an autoclave, and maintained at 150° C. for 40 h. The resulting crystals were discharged, washed with water twice, dried at 120° C. for 4 h, and calcined at 550° C. for 3 h, to give an intergrowth molecular sieve of ZSM-5, ZSM-23 and Y zeolite. It was found through XRD quantitative analysis that this intergrowth molecular sieve comprised 30.5 wt % of ZSM-23, 40.7 wt % of ZSM-5, and 28.8 wt % of Y zeolite. An intergrowth molecular sieve of ZSM-5, ZSM-23 and Y zeolite in hydrogen form, which is referred to as FH-22, was prepared according to the procedure as described in Example 1.

Example 23

33.3 g of sodium metasilicate was dissolved in 100 g of distilled water to form a solution A. 57.4 g of 40% silica sol was dissolved in 100 g of distilled water to form a solution B. 0.48 g of aluminum sulfate was dissolved in 20 ml of distilled water to form a solution C. The solution A and the solution C were separately slowly poured into the solution B while vigorously stirring. Next, 2.6 g of sodium hydroxide and 29.4 g of tetraethyl ammonium hydroxide (M) were added thereto, and then 1.2 g of mordenite as crystal seeds was added. The mixture was stirred for 20 min, and then was adjusted with diluted sulphuric acid to pH 11. Then water was added so that the resultant mixture had a molar ratio of Si:Al:Na:M:$H_2O$=1:0.005:0.6:0.2:40. The mixture was placed in an autoclave, and maintained at 160° C. for 40 h. The resulting crystals were discharged, washed with water twice, dried at 120° C. for 4 h, and calcined at 550° C. for 3 h, to give an intergrowth molecular sieve of β zeolite, Magadiite and mordenite. It was found through XRD quantitative analysis that this intergrowth molecular sieve comprised 54.5 wt % of β zeolite, 24.9 wt % of mordenite, and 20.6 wt % of Magadiite. An intergrowth molecular sieve of β zeolite, Magadiite and mordenite in hydrogen form, which is referred to as FH-23, was prepared according to the procedure as described in Example 1.

Example 24

33.3 g of sodium metasilicate was dissolved in 100 g of distilled water to form a solution A. 57.4 g of 40% silica sol was dissolved in 100 g of distilled water to form a solution B. 0.48 g of aluminum sulfate was dissolved in 20 ml of distilled water to form a solution C. The solution A and the solution C were separately slowly poured into the solution B while vigorously stirring. Next, 2.6 g of sodium hydroxide was added thereto, and then 1.2 g of β zeolite as crystal seeds was added. The mixture was stirred for 20 min, and then was adjusted with diluted sulphuric acid to pH 11. Then water was added so that the resultant mixture had a molar ratio of Si:Al:Na:$H_2O$=1:0.005:0.6:40. The mixture was placed in an autoclave, and maintained at 160° C. for 40 h. The resulting crystals were discharged, washed with water twice, dried at 120° C. for 4 h, and calcined at 550° C. for 3 h, to give an intergrowth molecular sieve of β zeolite and Magadiite. It was found through XRD quantitative analysis that this intergrowth molecular sieve comprised 55.4 wt % of β zeolite and 44.6 wt % of Magadiite. An intergrowth molecular sieve of β zeolite and Magadiite in hydrogen form, which is referred to as FH-24, was prepared according to the procedure as described in Example 1.

Example 25

33.3 g of sodium metasilicate was dissolved in 100 g of distilled water to form a solution A. 57.4 g of 40% silica sol was dissolved in 100 g of distilled water to form a solution B. 0.48 g of aluminum sulfate was dissolved in 20 ml of distilled water to form a solution C. The solution A and the solution C were separately slowly poured into the solution B while vigorously stirring. Next, 2.6 g of sodium hydroxide was added thereto, and then 1.2 g of mordenite as crystal seeds was added. The mixture was stirred for 20 min, and then was adjusted with diluted sulphuric acid to pH 11. Then water was added so that the resultant mixture had a molar ratio of Si:Al:Na:$H_2O$=1:0.005:0.6:40. The mixture was placed in an autoclave, and maintained at 180° C. for 40 h. The resulting crystals were discharged, washed with water twice, dried at 120° C. for 4 h, and calcined at 550° C. for 3 h, to give an intergrowth molecular sieve of mordenite and Magadiite. It was found through XRD quantitative analysis that this intergrowth molecular sieve comprised 30.8 wt % of mordenite and 69.2 wt % of Magadiite. An intergrowth molecular sieve of mordenite and Magadiite in hydrogen form, which is referred to as FH-25, was prepared according to the procedure as described in Example 1.

Example 26

33.3 g of sodium metasilicate was dissolved in 100 g of distilled water to form a solution A. 57.4 g of 40% silica sol was dissolved in 100 g of distilled water to form a solution B. 0.48 g of aluminum sulfate was dissolved in 20 ml of distilled water to form a solution C. The solution A and the solution C were separately slowly poured into the solution B while vigorously stirring. Next, 2.6 g of sodium hydroxide was added thereto, and then 1.2 g of β zeolite as crystal seeds was added. The mixture was stirred for 20 min, and then was adjusted with diluted sulphuric acid to pH 11. Then water was added so that the resultant mixture had a molar ratio of Si:Al:Na:$H_2O$=1:0.005:0.6:40. The mixture was placed in an autoclave, and maintained at 180° C. for 40 h. The resulting crystals were discharged, washed with water twice, dried at 120° C. for 4 h, and calcined at 550° C. for 3 h, to give an intergrowth molecular sieve of β zeolite and Magadiite. It was found through XRD quantitative analysis that this intergrowth molecular sieve comprised 40.6 wt % of β zeolite and 59.4 wt % of Magadiite. An intergrowth molecular sieve of β zeolite and Magadiite in hydrogen form, which is referred to as FH-26, was prepared according to the procedure as described in Example 1.

Example 27

284 g of sodium metasilicate was dissolved in 300 g of distilled water to form a solution A. 33.4 g of aluminum sulfate was dissolved in 100 g of distilled water to form a solution B. Then the solution B was slowly poured into the solution A while vigorously stirring, and then 24.4 g of ethylene diamine as templating agent M was added thereto. The mixture was stirred for 20 min, and then was adjusted with NaOH and diluted sulphuric acid to pH 12. Then water was added so that the resultant mixture had a molar ratio of Si:Al:M:$H_2O$:$OH^-$=1:0.1:0.4:40:1.2. The mixture was placed in an autoclave, and maintained at 180° C. for 40 h. The resulting crystals were discharged, washed with water twice, dried at 120° C. for 4 h, and calcined at 550° C. for 3 h, to give an intergrowth molecular sieve of ZSM-5, mordenite and analcite. It was found through XRD quantitative analysis that this intergrowth molecular sieve comprised 50.2 wt % of ZSM-5, 23.6 wt % of mordenite, and 26.2 wt % of analcite. An intergrowth molecular sieve of ZSM-5, mordenite and analcite in hydrogen form, which is referred to as FH-27, was prepared according to the procedure as described in Example 1.

Example 28

284 g of sodium metasilicate was dissolved in 300 g of distilled water to form a solution A. 16.7 g of aluminum sulfate was dissolved in 100 g of distilled water to form a solution B. Then the solution B was slowly poured into the solution A while vigorously stirring, and then 12.2 g of ethylene diamine and 29.4 g of tetraethyl ammonium hydroxide (mixed templating agents, referred to as M) were added thereto. The mixture was stirred for 20 min, and then was adjusted with diluted sulphuric acid to pH 11. Then water was added so that the resultant mixture had a molar ratio of Si:Al:M:$H_2O$=1:0.05:0.4:40. 3.0 g of β zeolite as crystal seeds was added thereto. After stirred for 30 min, the mixture was placed in an autoclave, and maintained at 160° C. for 40 h. The resulting crystals were discharged, washed with water twice, dried at 120° C. for 4 h, and calcined at 550° C. for 3 h, to give an intergrowth molecular sieve of ZSM-5, mordenite and β zeolite. It was found through XRD quantitative analysis that this intergrowth molecular sieve comprised 60.5 wt % of ZSM-5, 23.4 wt % of mordenite, and 16.1 wt % of β zeolite. An intergrowth molecular sieve of ZSM-5, mordenite and β zeolite in hydrogen form, which is referred to as FH-28, was prepared according to the procedure as described in Example 1.

Example 29

284 g of sodium metasilicate was dissolved in 300 g of distilled water to form a solution A. 33.4 g of aluminum sulfate was dissolved in 100 g of distilled water to form a solution B. Then the solution B was slowly poured into the solution A while vigorously stirring, and then 12.2 g of ethylene diamine and 29.4 g of tetraethyl ammonium hydroxide (mixed templating agents, referred to as M) were added thereto. The mixture was stirred for 20 min, and then was adjusted with diluted sulphuric acid to pH 11. Then water was added so that the resultant mixture had a molar ratio of Si:Al:M:$H_2O$=1:0.1:0.4:40. 2.8 g of Y zeolite as crystal seeds was added thereto. After stirred for 30 min, the mixture was placed in an autoclave, and maintained at 160° C. for 40 h. The resulting crystals were discharged, washed with water twice, dried at 120° C. for 4 h, and calcined at 550° C. for 3 h, to give an intergrowth molecular sieve of ZSM-5, mordenite and Y zeolite. It was found through XRD quantitative analysis that this intergrowth molecular sieve comprised 50.5 wt % of ZSM-5, 24.2 wt % of mordenite, and 25.3 wt % of Y zeolite. An intergrowth molecular sieve of ZSM-5, mordenite and Y zeolite in hydrogen form, which is referred to as FH-29, was prepared according to the procedure as described in Example 1.

Example 30

284 g of sodium metasilicate was dissolved in 300 g of distilled water to form a solution A. 16.7 g of aluminum sulfate was dissolved in 100 g of distilled water to form a solution B. Then the solution B was slowly poured into the solution A while vigorously stirring, and then 12.2 g of ethylene diamine and 19.9 g of hexamethylene imine (mixed templating agents, referred to as M) were added thereto. The mixture was stirred for 20 min, and then was adjusted with diluted sulphuric acid to pH 11. Then water was added so that the resultant mixture had a molar ratio of Si:Al:M:$H_2O$=1:0.05:0.4:40. 3.0 g of MCM-22 as crystal seeds was added thereto. After stirred for 30 min, the mixture was placed in an autoclave, and maintained at 150° C. for 40 h. The resulting crystals were discharged, washed with water twice, dried at 120° C. for 4 h, and calcined at 550° C. for 3 h, to give an intergrowth molecular sieve of ZSM-5, mordenite and MCM-22. It was found through XRD quantitative analysis that this intergrowth molecular sieve comprised 60.3 wt % of ZSM-5, 8.9 wt % of mordenite, and 30.8 wt % of MCM-22. An intergrowth molecular sieve of ZSM-5, mordenite and MCM-22 in hydrogen form, which is referred to as FH-30, was prepared according to the procedure as described in Example 1.

Example 31

33.3 g of sodium metasilicate was dissolved in 100 g of distilled water to form a solution A. 57.4 g of 40% silica sol was dissolved in 100 g of distilled water to form a solution B. The solution A was slowly poured into the solution B, and the mixture was vigorously stirred for 1 h. Next, the mixture was adjusted with diluted sulphuric acid to pH 11. Then water was added so that the resultant mixture had a molar ratio of Si:Al:Na:$H_2O$=1:0.002:0.5:40. The mixture was placed in an autoclave, and maintained at 180° C. for 40 h. The resulting crystals were discharged, washed with water twice, dried at 120° C. for 4 h, and calcined at 550° C. for 3 h, to give an intergrowth molecular sieve of ZSM-5 and Magadiite. It was found through XRD quantitative analysis that this intergrowth molecular sieve comprised 40.6 wt % of ZSM-5 and 59.4 wt % of Magadiite. An intergrowth molecular sieve of ZSM-5 and Magadiite in hydrogen form, which is referred to as FH-31, was prepared according to the procedure as described in Example 1.

Examples 32 to 37

Following the procedure as described in Example 27, a series of intergrowth molecular sieves of ZSM-5, mordenite and analcite were respectively synthesized by using the raw materials as shown in the Table 9 below in the molar ratio as shown in the Table 1 below. The contents of ZSM-5, mordenite and analcite in the intergrowth molecular sieves are shown in the Table 2 below.

TABLE 1

| Example | Molar ratio of the components in the solution | Sample No. |
|---|---|---|
| Example 32 | Si:Al:M:$H_2O$:$OH^{-1}$ = 1:0.005:0.4:40:5 | FH-32 |
| Example 33 | Si:Al:M:$H_2O$:$OH^{-1}$ = 1:0.01:0.4:40:0.01 | FH-33 |
| Example 34 | Si:Al:M:$H_2O$:$OH^{-1}$ = 1:0.1:0.1:50:0.001 | FH-34 |
| Example 35 | Si:Al:M:$H_2O$:$OH^{-1}$ = 1:0.125:0.2:40:0.5 | FH-35 |
| Example 36 | Si:Al:M:$H_2O$:$OH^{-1}$ = 1:0.167:0:60:2 | FH-36 |
| Example 37 | Si:Al:M:$H_2O$:$OH^{-1}$ = 1:0.2:0.01:80:4 | FH-37 |

TABLE 2

| Sample No. | $SiO_2/Al_2O_3$ (molar ratio) | Content of ZSM-5 (wt %) | Content of mordenite (wt %) | Content of analcite (wt %) |
|---|---|---|---|---|
| FH-32 | 400 | 96.2 | 1.8 | 2.0 |
| FH-33 | 200 | 95.8 | 2.4 | 1.8 |
| FH-34 | 20 | 88.2 | 6.5 | 5.3 |
| FH-35 | 16 | 65.4 | 22.0 | 12.6 |
| FH-36 | 12 | 33.6 | 25.3 | 41.1 |
| FH-37 | 10 | 12.3 | 11.3 | 76.4 |

Examples 38 to 43

Following the procedure as described in Example 28, a series of intergrowth molecular sieves of ZSM-5, mordenite and β zeolite were respectively synthesized by using the raw materials as shown in the Table 9 below in the molar ratio as shown in the Table 3 below (if mixed templating agents were used, they were used in a ratio of 1:1 or 1:1:1, similarly hereinafter). The contents of ZSM-5, mordenite and β zeolite in the intergrowth molecular sieves are shown in the Table 4 below.

TABLE 3

| Example | Molar ratio of the components in the solution | Sample No. |
| --- | --- | --- |
| Example 38 | Si:Al:M:$H_2O$:$OH^{-1}$ = 1:0.004:0.4:40:1.5 | FH-38 |
| Example 39 | Si:Al:M:$H_2O$:$OH^{-1}$ = 1:0.01:0.4:40:0.01 | FH-39 |
| Example 40 | Si:Al:M:$H_2O$:$OH^{-1}$ = 1:0.125:0.2:40:0.5 | FH-40 |
| Example 41 | Si:Al:M:$H_2O$:$OH^{-1}$ = 1:0.143:0.1:40:1.2 | FH-41 |
| Example 42 | Si:Al:M:$H_2O$:$OH^{-1}$ = 1:0.167:0:60:2 | FH-42 |
| Example 43 | Si:Al:M:$H_2O$:$OH^{-1}$ = 1:0.25:0.4:100:3 | FH-43 |

TABLE 4

| Sample No. | $SiO_2/Al_2O_3$ (molar ratio) | Content of ZSM-5 (wt %) | Content of mordenite (wt %) | Content of β zeolite (wt %) |
| --- | --- | --- | --- | --- |
| FH-38 | 500 | 60.5 | 22.4 | 17.1 |
| FH-39 | 200 | 97.2 | 1.2 | 1.6 |
| FH-40 | 16 | 84.4 | 8.0 | 7.6 |
| FH-41 | 14 | 48.7 | 40.5 | 10.8 |
| FH-42 | 12 | 32.1 | 54.5 | 14.4 |
| FH-43 | 8 | 14.5 | 73.3 | 12.2 |

Examples 44 to 49

Following the procedure as described in Example 29, a series of intergrowth molecular sieves of ZSM-5, mordenite and Y zeolite were respectively synthesized by using the raw materials as shown in the Table 9 below in the molar ratio as shown in the Table 5 below. The contents of ZSM-5, mordenite and Y zeolite in the intergrowth molecular sieves are shown in the Table 6 below.

TABLE 5

| Example | Molar ratio of the components in the solution | Sample No. |
| --- | --- | --- |
| Example 44 | Si:Al:M:$H_2O$:$OH^{-1}$ = 1:0.005:0.4:40:1.5 | FH-44 |
| Example 45 | Si:Al:M:$H_2O$:$OH^{-1}$ = 1:0.01:0.4:40:0.01 | FH-45 |
| Example 46 | Si:Al:M:$H_2O$:$OH^{-1}$ = 1:0.1:0.1:50:0.001 | FH-46 |
| Example 47 | Si:Al:M:$H_2O$:$OH^{-1}$ = 1:0.125:0.2:40:0.5 | FH-47 |
| Example 48 | Si:Al:M:$H_2O$:$OH^{-1}$ = 1:0.143:0.1:40:1.2 | FH-48 |
| Example 49 | Si:Al:M:$H_2O$:$OH^{-1}$ = 1:0.25:0.01:80:1 | FH-49 |

TABLE 6

| Sample No. | Content of ZSM-5 (wt %) | Content of mordenite (wt %) | Content of Y zeolite (wt %) |
| --- | --- | --- | --- |
| FH-44 | 50.5 | 24.2 | 25.3 |
| FH-45 | 97.1 | 1.4 | 1.5 |
| FH-46 | 88.3 | 6.5 | 5.2 |
| FH-47 | 76.2 | 12.3 | 11.5 |
| FH-48 | 40.4 | 38.5 | 21.1 |
| FH-49 | 22.3 | 45.8 | 31.9 |

Examples 50 to 55

Following the procedure as described in Example 30, a series of intergrowth molecular sieves of ZSM-5, mordenite and MCM-22 were respectively synthesized by using the raw materials as shown in the Table 9 below in the molar ratio as shown in the Table 7 below. The contents of ZSM-5, mordenite and MCM-22 in the intergrowth molecular sieves are shown in the Table 8 below.

TABLE 7

| Example | Molar ratio of the components in the solution | Sample No. |
| --- | --- | --- |
| Example 50 | Si:Al:M:$H_2O$:$OH^{-1}$ = 1:0.005:0.4:40:1 | FH-50 |
| Example 51 | Si:Al:M:$H_2O$:$OH^{-1}$ = 1:0.1:0.1:50:0.001 | FH-51 |
| Example 52 | Si:Al:M:$H_2O$:$OH^{-1}$ = 1:0.05:2:30:0.1 | FH-52 |
| Example 53 | Si:Al:M:$H_2O$:$OH^{-1}$ = 1:0.05:3:20:1.8 | FH-53 |
| Example 54 | Si:Al:M:$H_2O$:$OH^{-1}$ = 1:0.167:0:60:2 | FH-54 |
| Example 55 | Si:Al:M:$H_2O$:$OH^{-1}$ = 1:0.25:0.4:100:1.3 | FH-55 |

TABLE 8

| Sample No. | Content of ZSM-5 (wt %) | Content of mordenite (wt %) | Content of MCM-22 (wt %) |
| --- | --- | --- | --- |
| FH-50 | 60.3 | 8.9 | 30.8 |
| FH-51 | 96.8 | 1.4 | 1.8 |
| FH-52 | 56.2 | 24.3 | 19.5 |
| FH-53 | 33.6 | 25.3 | 41.1 |
| FH-54 | 40.3 | 7.8 | 51.9 |
| FH-55 | 16.7 | 70.3 | 13.0 |

TABLE 9

| Sample No. | Silicon source | Aluminum source | Templating agent | Base source | Acid |
| --- | --- | --- | --- | --- | --- |
| FH-32 | sodium metasilicate | aluminum sulfate | ethylene diamine | Sodium hydroxide | diluted sulfuric acid |
| FH-33 | silica sol | sodium metaaluminate | n-butyl amine | Sodium hydroxide | diluted hydrochloric acid |
| FH-34 | amorphous silica | pseudoboehmite | n-butyl amine | Sodium hydroxide | diluted nitric acid |
| FH-35 | silica gel | bauxite | n-butyl amine | Sodium hydroxide | oxalic acid |
| FH-36 | diatomite | aluminum hydroxide sol | ethylene diamine | Sodium hydroxide | acetic acid |

TABLE 9-continued

| Sample No. | Silicon source | Aluminum source | Templating agent | Base source | Acid |
|---|---|---|---|---|---|
| FH-37 | sodium silicate | aluminum sulfate | ammonia water | Sodium hydroxide | diluted hydrochloric acid |
| FH-38 | tetraethyl orthosilicate | aluminum sulfate | ethylene diamine | Sodium hydroxide | diluted hydrochloric acid |
| FH-39 | silica sol | aluminum nitrate | tetraethyl ammonium hydroxide | Sodium hydroxide | diluted hydrochloric acid |
| FH-40 | silica sol | aluminum trichloride | ethyl amine | Sodium hydroxide | diluted sulfuric acid |
| FH-41 | silica sol | sodium aluminate | triethyl amine | Sodium hydroxide | diluted sulfuric acid |
| FH-42 | silica sol | aluminum sulfate | tetraethyl ammonium hydroxide | Sodium hydroxide | diluted sulfuric acid |
| FH-43 | silica sol | aluminum sulfate | ethyl amine | potassium hydroxide | diluted sulfuric acid |
| FH-44 | silica sol | sodium aluminate | tetrapropyl ammonium hydroxide | potassium hydroxide | diluted hydrochloric acid |
| FH-45 | sodium metasilicate | sodium aluminate | tetrapropyl ammonium bromide | potassium hydroxide | diluted hydrochloric acid |
| FH-46 | sodium metasilicate | sodium aluminate | tetraethyl ammonium hydroxide | potassium hydroxide | diluted hydrochloric acid |
| FH-47 | sodium metasilicate | sodium aluminate | tetraethyl ammonium bromide | potassium hydroxide | diluted hydrochloric acid |
| FH-48 | sodium metasilicate | sodium aluminate | n-butyl amine and hexamethylene imine | potassium hydroxide | diluted sulfuric acid |
| FH-49 | sodium metasilicate, silica sol | sodium metaaluminate | ethyl amine, ethylene diamine and hexamethylene imine | potassium hydroxide | diluted nitric acid |
| FH-50 | tetraethyl orthosilicate, silica sol | sodium metaaluminate | ammonia water and hexamethylene imine | potassium hydroxide, Sodium hydroxide | diluted sulfuric acid, diluted hydrochloric acid |
| FH-51 | tetraethyl orthosilicate | sodium metaaluminate, aluminum sulfate | tetrapropyl ammonium hydroxide, n-butyl amine and hexamethylene imine | potassium hydroxide, Sodium hydroxide | diluted sulfuric acid, diluted hydrochloric acid |
| FH-52 | tetraethyl orthosilicate | sodium metaaluminate, aluminum sulfate | tetraethyl ammonium hydroxide | potassium hydroxide, Sodium hydroxide | diluted sulfuric acid, diluted hydrochloric acid |
| FH-53 | tetraethyl orthosilicate | sodium metaaluminate | triethyl amine, hexamethylene imine | potassium hydroxide | diluted nitric acid |
| FH-54 | sodium silicate | aluminum sulfate | hexamethylene imine | Sodium hydroxide | diluted nitric acid |
| FH-55 | sodium silicate | aluminum sulfate | ammonia water, tetrabutyl ammonium bromide and hexamethylene imine | Sodium hydroxide | diluted nitric acid |

Examples 56 to 64

The intergrowth molecular sieve of ZSM-5 and mordenite in hydrogen form as prepared in Example 1, the intergrowth molecular sieve of ZSM-5 and β zeolite in hydrogen form as prepared in Example 2, and the intergrowth molecular sieve of ZSM-5 and Y zeolite in hydrogen form as prepared in Example 3 were mixed in certain proportions, to give physical mixtures, as shown in the Table 10 below.

The intergrowth molecular sieve of ZSM-5, mordenite and analcite in hydrogen form as prepared in Example 27, the intergrowth molecular sieve of ZSM-5, mordenite and β zeolite in hydrogen form as prepared in Example 28, the intergrowth molecular sieve of ZSM-5, mordenite and Y zeolite in hydrogen form as prepared in Example 29, and the intergrowth molecular sieve of ZSM-5, mordenite and MCM-22 in hydrogen form as prepared in Example 24 were mixed in certain proportions, to give physical mixtures, as shown in the Table 10 below.

TABLE 10

| Example | Intergrowth molecular sieve type | Ratio by weight | Sample No. |
|---|---|---|---|
| Example 56 | ZSM-5/mordenite + ZSM-5/β zeolite | 1:1 | HH-56 |
| Example 57 | ZSM-5/mordenite + ZSM-5/Y zeolite | 1:1 | HH-57 |
| Example 58 | ZSM-5/β zeolite + ZSM-5/Y zeolite | 1:1 | HH-58 |
| Example 59 | ZSM-5/mordenite + ZSM-5/β zeolite + ZSM-5/Y zeolite | 1:1:1 | HH-59 |
| Example 60 | ZSM-5/mordenite/analcite + ZSM-5/mordenite/β zeolite | 1:1 | HH-60 |
| Example 61 | ZSM-5/mordenite/β zeolite + ZSM-5/mordenite/Y zeolite | 1:1 | HH-61 |
| Example 62 | ZSM-5/mordenite/Y zeolite + ZSM-5/mordenite/MCM-22 | 1:1 | HH-62 |
| Example 63 | ZSM-5/mordenite/analcite + ZSM-5/mordenite/β zeolite + ZSM-5/mordenite/Y zeolite | 1:1:1 | HH-63 |
| Example 64 | ZSM-5/mordenite/analcite + ZSM-5/mordenite/β zeolite + ZSM-5/mordenite/Y zeolite + ZSM-5/mordenite/MCM-22 | 1:1:1:1 | HH-64 |

Example 65

20 g of the intergrowth molecular sieve of ZSM-5 and mordenite in hydrogen form as prepared in Example 1 was uniformly mixed with 58 ml of 0.05M aqueous solution of lanthanum nitrate and 64.5 ml of 0.1M phosphoric acid, and then the mixture was evaporated at 70° C. to dryness while stirring. The solid residue was dried at 120° C. for 3 h, and then calcined at 550° C. for 3 h, to give a ZSM-5/mordenite intergrowth molecular sieve modified with lanthanum and phosphorus. The modified molecular sieve was pressed into tablets, crushed, and sieved. Then particles of 20 to 40 mesh were loaded into a fixed bed reactor having an inner diameter of 12 mm, and evaluated under the following conditions: reaction temperature of 650° C., reaction pressure of 0.02 MPa (gauge), weight hourly space velocity of naphtha of 1 $h^{-1}$, and weight ratio of water to naphtha of 2:1. The results are shown in the Table 11 below.

Example 66

20 g of the intergrowth molecular sieve of ZSM-5 and β zeolite in hydrogen form as prepared in Example 2 was uniformly mixed with 58 ml of 0.05M aqueous solution of lanthanum nitrate and 64.5 ml of 0.1M phosphoric acid, and then the mixture was evaporated at 70° C. to dryness while stirring. The solid residue was dried at 120° C. for 3 h, and then calcined at 550° C. for 3 h, to give a ZSM-5/β zeolite intergrowth molecular sieve modified with lanthanum and phosphorus. The modified molecular sieve was mixed with alumina and Sesbania cannabina powder according to a weight ratio of 12:7:1, and then 20 ml of 5 vol % diluted nitric acid was added thereto, and the mixture was homogenously mixed and then extruded. The extrudates were dried at 120° C. for 3 h, and then calcined in a muffle furnace at 550° C. for 4 h. The extrudates were taken out and then crushed and sieved. Particles of 20 to 40 mesh were loaded into a fixed bed reactor having an inner diameter of 12 mm, and evaluated under the following conditions: reaction temperature of 650° C., reaction pressure of 0.02 MPa (gauge), weight hourly space velocity of naphtha of 1 $h^{-1}$, and weight ratio of water to naphtha of 2:1. The results are shown in the Table 11 below.

Example 67

200 g of the intergrowth molecular sieve of ZSM-5 and Y zeolite in hydrogen form as prepared in Example 3 was uniformly mixed with 580 ml of 0.05M aqueous solution of lanthanum nitrate and 645 ml of 0.1M phosphoric acid, and then the mixture was evaporated at 70° C. to dryness while stirring. The solid residue was dried at 120° C. for 3 h, and then calcined at 550° C. for 3 h, to give a ZSM-5/Y zeolite intergrowth molecular sieve modified with lanthanum and phosphorus. The modified molecular sieve was mixed with silica sol having a solid content of 40 wt % according to a weight ratio of 1:1, and then the mixture was spray dried. The dried mixture was calcined in a muffle furnace at 550° C. for 4 h and then taken out and sieved. Particles of 10 to 150 microns were loaded into a fluidized bed reactor having an inner diameter of 50 mm, and evaluated under the following conditions: reaction temperature of 650° C., reaction pressure of 0.02 MPa (gauge), weight hourly space velocity of naphtha of 1 $h^{-1}$, and weight ratio of water to naphtha of 2:1. The results are shown in the Table 11 below.

Example 68

200 g of the ZSM-5/mordenite/β zeolite intergrowth molecular sieve in hydrogen form as prepared in Example 28 was uniformly mixed with 580 ml of 0.05M aqueous solution of lanthanum nitrate and 645 ml of 0.1M phosphoric acid, and then the mixture was evaporated at 70° C. to dryness while stirring. The solid residue was dried at 120° C. for 3 h, and then calcined at 550° C. for 3 h, to give a ZSM-5/mordenite/β zeolite intergrowth molecular sieve modified with lanthanum and phosphorus. The modified molecular sieve was mixed with silica sol having a solid content of 40 wt % and kaolin according to a weight ratio of 6:3:1, and then the mixture was spray dried. The dried mixture was calcined in a muffle furnace at 550° C. for 4 h and then taken out and sieved. Particles of 10 to 150 microns in diameter were placed into an autoclave and treated at 180° C. with ethylene diamine vapor for 60 h, to give a catalyst having binder converted into crystal. So-prepared catalyst was loaded into a fluidized bed reactor having an inner diameter of 50 mm, and evaluated under the following conditions: reaction temperature of 650° C., reaction pressure of 0.02 MPa (gauge), weight hourly space velocity of naphtha of 1 $h^{-1}$, and weight ratio of water to naphtha of 2:1. The results are shown in the Table 11 below.

Examples 69 to 81

The intergrowth molecular sieves as prepared in Examples 4 to 16 were modified and evaluated following the procedure as described in Example 66. So-prepared catalyst compositions and evaluation results are shown in the Table 11 below.

TABLE 11

| Example | Intergrowth molecular sieve | Type and content of modifying elements (wt %) | Ethylene yield (wt %) | Propylene yield (wt %) | Yield of ethylene plus propylene (wt %) |
| --- | --- | --- | --- | --- | --- |
| Example 65 | FH-1 | 2% La + 1% P | 27.2 | 29.4 | 56.6 |
| Example 66 | FH-2 | 2% La + 1% P | 26.4 | 28.9 | 55.3 |
| Example 67 | FH-3 | 2% La + 1% P | 26.5 | 28.9 | 55.4 |
| Example 68 | FH-28 | 2% La + 1% P | 29.0 | 27.5 | 56.5 |
| Example 69 | FH-4 | 2% La + 1% P | 28.56 | 26.14 | 54.70 |
| Example 70 | FH-5 | 6% Ce + 0.5% B | 28.07 | 25.29 | 53.36 |
| Example 71 | FH-6 | 10% La + 1% Cu | 30.13 | 22.94 | 53.07 |
| Example 72 | FH-7 | 5% La + 2% Zn | 24.35 | 21.31 | 45.66 |
| Example 73 | FH-8 | 15% La + 1% Mg | 28.02 | 24.22 | 52.24 |
| Example 74 | FH-9 | 1% La + 0.5% K | 26.65 | 24.54 | 51.19 |

TABLE 11-continued

| Example | Intergrowth molecular sieve | Type and content of modifying elements (wt %) | Ethylene yield (wt %) | Propylene yield (wt %) | Yield of ethylene plus propylene (wt %) |
|---|---|---|---|---|---|
| Example 75 | FH-10 | 0.5% P + 0.5% B | 25.44 | 24.40 | 49.84 |
| Example 76 | FH-11 | 0.2% La + 0.2Bi | 25.43 | 21.38 | 46.81 |
| Example 77 | FH-12 | 2% La + 2% Ga | 26.15 | 22.68 | 48.83 |
| Example 78 | FH-13 | 10% Ce + 1% Ca | 28.98 | 23.21 | 53.19 |
| Example 79 | FH-14 | 4% Ce + 4% Li | 27.23 | 25.32 | 52.55 |
| Example 80 | FH-15 | 5% La + 5% Cd | 25.12 | 26.87 | 51.99 |
| Example 81 | FH-16 | 2% La + 0.2% Ag | 27.32 | 27.45 | 54.77 |

Example 82

200 g of the ZSM-5/β zeolite/ZSM-23 intergrowth molecular sieve in hydrogen form as prepared in Example 17 was uniformly mixed with 580 ml of 0.1M aqueous solution of lanthanum nitrate, 645 ml of 0.1M phosphoric acid and 363 ml of 0.5M boric acid, and then the mixture was evaporated at 70° C. to dryness while stirring. The solid residue was dried and then calcined to give a ZSM-5/β zeolite/ZSM-23 intergrowth molecular sieve modified with lanthanum, phosphorus and boron. Molded catalyst composition was prepared and evaluated following the procedure as described in Example 66. The results are shown in the Table 12 below.

Examples 83 to 88

The intergrowth molecular sieves as prepared in Examples 18 to 23 were modified and evaluated following the procedure as described in Example 66. So-prepared catalyst compositions and evaluation results are shown in the Table 12 below.

of lanthanum nitrate, 645 ml of 0.1M phosphoric acid, 363 ml of 0.5M boric acid and 315 ml of 0.1M copper nitrate, and then the mixture was evaporated at 70° C. to dryness while stirring. The solid residue was dried and then calcined to give a ZSM-5/mordenite/Y zeolite intergrowth molecular sieve modified with lanthanum, phosphorus, boron and copper. The catalyst composition was evaluated following the procedure as described in Example 67. The results are shown in the Table 13 below.

Examples 90 to 96

The intergrowth molecular sieves as prepared in Examples 24 to 30 were modified and evaluated following the procedure as described in Example 67. So-prepared catalyst compositions and evaluation results are shown in the Table 13 below.

TABLE 12

| Example | Intergrowth molecular sieve | Type and content of modifying elements (wt %) | Ethylene yield (wt %) | Propylene yield (wt %) | Yield of ethylene plus propylene (wt %) |
|---|---|---|---|---|---|
| Example 82 | FH-17 | 2% La + 1% P + 1% B | 26.67 | 27.24 | 54.01 |
| Example 83 | FH-18 | 2% Ce + 2% P + 1% Cu | 26.22 | 27.38 | 53.60 |
| Example 84 | FH-19 | 2% La + 1% P + 1% Zn | 26.94 | 27.67 | 54.61 |
| Example 85 | FH-20 | 2% La + 1% P + 1% Mg | 28.32 | 24.51 | 52.83 |
| Example 86 | FH-21 | 2% La + 1% P + 1% K | 29.13 | 22.63 | 51.66 |
| Example 87 | FH-22 | 2% La + 1% Bi + 1% B | 28.56 | 22.88 | 51.44 |
| Example 88 | FH-23 | 2% La + 1% P + 1% Ga | 26.35 | 23.71 | 50.06 |

Example 89

200 g of the ZSM-5/mordenite/Y zeolite intergrowth molecular sieve in hydrogen form as prepared in Example 29 was uniformly mixed with 580 ml of 0.1M aqueous solution

TABLE 13

| Example | Intergrowth molecular sieve | Type and content of modifying elements (wt %) | Ethylene yield (wt %) | Propylene yield (wt %) | Yield of ethylene plus propylene (wt %) |
|---|---|---|---|---|---|
| Example 89 | FH-29 | 2% La + 1% P + 1% B + 1% Cu | 27.33 | 27.25 | 54.58 |
| Example 90 | FH-24 | 2% La + 1% P + 1% B + 1% Zn | 27.65 | 25.71 | 53.36 |
| Example 91 | FH-25 | 2% La + 1% P + 1% B + 1% Mg | 27.82 | 26.17 | 53.99 |
| Example 92 | FH-26 | 2% La + 1% P + 1% B + 1% K | 28.56 | 24.85 | 53.41 |
| Example 93 | FH-27 | 2% Ce + 1% Bi + 1% Ga + 0.5% Cd | 29.24 | 23.48 | 52.72 |
| Example 94 | FH-28 | 2% Ce + 1% Bi + 1% Ga + 0.5% Ag | 29.63 | 21.42 | 51.05 |
| Example 95 | FH-29 | 2% La + 1% P + 1% B + 1% Ca | 25.19 | 24.45 | 49.64 |
| Example 96 | FH-30 | 2% La + 1% P + 1% B + 1% Li | 24.68 | 22.78 | 47.46 |

Example 97

200 g of the ZSM-5/Magadiite intergrowth molecular sieve in hydrogen form as prepared in Example 31 was uniformly mixed with 580 ml of 0.1M lanthanum nitrate, 645 ml of 0.1M phosphoric acid, 383 ml of 0.5M boric acid, 315 ml of 0.1M copper nitrate, and 310 ml of 0.1M zinc nitrate, and then the mixture was evaporated at 70° C. to dryness while stirring. The solid residue was dried and then calcined to give a ZSM-5/Magadiite intergrowth molecular sieve modified with lanthanum, phosphorus, boron, copper and zinc. The catalyst composition was evaluated following the procedure as described in Example 68. The results are shown in the Table 14 below.

Examples 98 to 103

The intergrowth molecular sieves as prepared in Examples 56 to 61 were modified and evaluated following the procedure as described in Example 68. So-prepared catalysts and evaluation results are shown in the Table 14 below.

TABLE 14

| Example | Intergrowth molecular sieve | Type and content of modifying elements (wt %) | Ethylene yield (wt %) | Propylene yield (wt %) | Yield of ethylene plus propylene (wt %) |
| --- | --- | --- | --- | --- | --- |
| Example 97  | FH-31 | 2% La + 1% P + 1% B + 1% Cu + 1% Zn | 26.85 | 27.18 | 54.03 |
| Example 98  | FH-56 | 2% La + 1% P + 1% B + 1% Cu + 1% Mg | 26.24 | 27.43 | 53.67 |
| Example 99  | FH-57 | 2% La + 1% P + 1% B + 1% Cu + 1% K  | 26.96 | 27.77 | 54.73 |
| Example 100 | FH-58 | 2% Ce + 1% Bi + 1% B + 1% Cu + 1% Li | 28.42 | 24.37 | 52.79 |
| Example 101 | FH-59 | 2% Ce + 1% P + 1% B + 1% Cu + 1% Ca | 29.12 | 22.62 | 51.74 |
| Example 102 | FH-60 | 2% La + 1% P + 1% B + 1% Cu + 1% Ba | 28.56 | 22.93 | 51.49 |
| Example 103 | FH-61 | 2% Pr + 1% P + 1% Ga + 1% Ag + 1% Cd | 26.22 | 23.64 | 49.86 |

Examples 104 to 110

The intergrowth molecular sieves as prepared in Examples 62 to 64 and Examples 7 to 10 were modified and evaluated following the procedure as described in Example 67. So-prepared catalysts and evaluation results are shown in the Table 15 below.

TABLE 15

| Example | Intergrowth molecular sieve | Type and content of modifying elements (wt %) | Ethylene yield (wt %) | Propylene yield (wt %) | Yield of ethylene plus propylene (wt %) |
| --- | --- | --- | --- | --- | --- |
| Example 104 | FH-62 | 2% La + 1% P + 1% B + 1% Cu + 1% Zn + 1% Mg | 27.85 | 27.18 | 55.03 |
| Example 105 | FH-63 | 2% La + 1% P + 1% B + 1% Cu + 1% Mg + 1% Ti | 27.24 | 27.43 | 54.67 |
| Example 106 | FH-64 | 2% La + 1% P + 1% B + 1% Cu + 1% K + 1% Zr | 27.96 | 27.77 | 55.73 |
| Example 107 | FH-7  | 2% Ce + 1% Bi + 1% B + 1% Cu + 1% Li + 1% V | 28.42 | 24.37 | 52.79 |
| Example 108 | FH-8  | 2% Ce + 1% P + 1% B + 1% Cu + 1% Ca + 1% Nb | 29.12 | 22.62 | 51.74 |
| Example 109 | FH-9  | 2% La + 1% P + 1% B + 1% Cu + 1% Ba + 1% K | 28.56 | 22.93 | 51.49 |
| Example 110 | FH-10 | 2% Pr + 1% P + 1% Ga + 1% Ag + 1% Cd + 1% Ti | 26.22 | 23.64 | 49.86 |

Examples 111 to 124

The intergrowth molecular sieves as prepared in Examples 14 to 27 were modified and evaluated following the procedure as described in Example 66. So-prepared catalyst compositions and evaluation results are shown in the Table 16 below.

TABLE 16

| Example | Intergrowth molecular sieve | Type and content of modifying elements (wt %) | Ethylene yield (wt %) | Propylene yield (wt %) | Yield of ethylene plus propylene (wt %) |
| --- | --- | --- | --- | --- | --- |
| Example 111 | FH-14 | 2% La + 1% P + 1% B + 1% Cu + 1% Zn + 1% Mg + 1% K | 21.98 | 28.64 | 50.62 |
| Example 112 | FH-15 | 2% La + 1% P + 1% B + 1% Cu + 1% Zn + 1% Mg + 1% Ti | 23.91 | 30.17 | 54.08 |

TABLE 16-continued

| Example | Intergrowth molecular sieve | Type and content of modifying elements (wt %) | Ethylene yield (wt %) | Propylene yield (wt %) | Yield of ethylene plus propylene (wt %) |
|---|---|---|---|---|---|
| Example 113 | FH-16 | 2% La + 1% P + 1% B + 1% Cu + 1% Cd + 1% K + 1% Zr | 23.65 | 24.72 | 48.37 |
| Example 114 | FH-17 | 2% Ce + 1% Bi + 1% B + 1% Cu + 1% Li + 1% V | 30.87 | 23.68 | 54.55 |
| Example 115 | FH-18 | 2% Ce + 1% P + 1% B + 1% Cu + 1% Ag + 1% Ca + 1% Nb | 29.74 | 23.25 | 52.99 |
| Example 116 | FH-19 | 2% La + 1% P + 1% B + 1% Cu + 1% Zn + 1% Ba + 1% K + 1% Ti | 22.46 | 27.33 | 49.79 |
| Example 117 | FH-20 | 2% Pr + 1% P + 1% Ga + 1% Ag + 1% Cd + 1% Mg + 1% K + 1% Ti | 18.21 | 29.64 | 47.85 |
| Example 118 | FH-21 | 2% La + 1% P + 1% B + 1% Cu + 1% Zn + 1% Mg + 1% K + 1% Ti + 1% V | 23.42 | 26.39 | 49.81 |
| Example 119 | FH-22 | 2% La + 1% P + 1% B + 1% Cu + 1% Zn + 1% Mg + 1% K + 1% Ti + 1% Nb | 28.74 | 22.92 | 51.66 |
| Example 120 | FH-23 | 2% La + 2% Ce + 1% P + 1% B + 1% Cu + 1% Zn + 1% Mg + 1% K + 1% Ti + 1% V | 31.85 | 23.76 | 55.61 |
| Example 121 | FH-24 | 2% La + 1% P + 1% B + 1% Cu + 1% Zn + 1% Ag + 1% Mg + 1% K + 1% Ti + 1% V | 25.71 | 28.95 | 54.66 |
| Example 122 | FH-25 | 2% La + 1% P + 1% Bi + 1% B + 1% Cu + 1% Zn + 1% Ag + 1% Mg + 1% K + 1% Ti + 1% V | 30.89 | 24.60 | 55.49 |
| Example 123 | FH-26 | 2% La + 2% Ce + 1% P + 1% Bi + 1% B + 1% Cu + 1% Zn + 1% Cd + 1% Mg + 1% K + 1% Ti + 1% V + 1% Li | 30.32 | 26.53 | 56.85 |
| Example 124 | FH-27 | 2% La + 2% Ce + 1% P + 1% Bi + 1% B + 1% Ga + 1% Cu + 1% Zn + 1% Cd + 1% Mg + 1% K + 1% Ti + 1% V + 1% Li | 30.72 | 26.48 | 57.20 |

Examples 125 to 128

The catalyst composition as prepared in Example 65 was evaluated under conditions: reaction pressure of 0.02 MPa; catalyst load of 1 g naphtha/gCatalyst·h; weight ratio of water to naphtha of 2:1; and reaction temperatures of 550° C., 580° C., 630° C., and 700° C., respectively. The results are shown in the Table 17.

Examples 129 to 133

The catalyst composition as prepared in Example 66 was evaluated under conditions: reaction temperature of 650° C.; catalyst load of 1 g naphtha/gCatalyst·h; weight ratio of water to naphtha of 3:1; and reaction pressures of 0.5 MPa, 0.2 MPa, 0.05 MPa, 0.01 MPa, and 0.001 MPa, respectively. The results are shown in the Table 17.

Examples 134 to 138

The catalyst composition as prepared in Example 67 was evaluated under conditions: reaction temperature of 650° C.; reaction pressure of 0.02 MPa; weight ratio of water to naphtha of 3:1; and catalyst load of 4 g naphtha/gCatalyst·h, 2 g naphtha/gCatalyst·h, 1 g naphtha/gCatalyst·h, 0.5 g naphtha/gCatalyst·h, and 0.1 g naphtha/gCatalyst·h, respectively. The results are shown in the Table 17.

Examples 139 to 142

The catalyst composition as prepared in Example 68 was evaluated under conditions: reaction temperature of 650° C.; reaction pressure of 0.02 MPa; catalyst load of 1 g naphtha/gCatalyst·h; and weight ratio of water to naphtha of 4:1, 2:1, 0.5:1, and 0.1:1, respectively. The results are shown in the Table 17.

TABLE 17

| Example | Ethylene yield (wt %) | Propylene yield (wt %) | Yield of ethylene plus propylene (wt %) |
|---|---|---|---|
| Example 125 | 20.35 | 25.47 | 45.82 |
| Example 126 | 21.63 | 26.27 | 47.90 |
| Example 127 | 30.33 | 27.25 | 57.58 |
| Example 128 | 32.27 | 21.69 | 53.96 |
| Example 129 | 27.93 | 23.67 | 51.60 |
| Example 130 | 24.81 | 27.73 | 52.54 |
| Example 131 | 28.27 | 24.82 | 53.09 |
| Example 132 | 32.12 | 23.64 | 55.76 |
| Example 133 | 30.54 | 28.67 | 59.21 |
| Example 134 | 25.57 | 25.16 | 50.73 |
| Example 135 | 27.41 | 24.69 | 52.10 |
| Example 136 | 32.47 | 22.92 | 55.39 |
| Example 137 | 30.24 | 28.25 | 58.49 |
| Example 138 | 29.27 | 23.15 | 52.42 |
| Example 139 | 34.98 | 24.69 | 59.77 |
| Example 140 | 32.37 | 25.23 | 57.60 |
| Example 141 | 31.20 | 25.34 | 56.54 |
| Example 142 | 28.79 | 23.18 | 51.97 |

Comparative Example 1

A ZSM-5 molecular sieve having a $SiO_2/Al_2O_3$ molar ratio of 40, manufactured by Shanghai Research Institute of Petrochemical Technology, Sinopec, was modified according to the procedure as described in Example 66, to give a ZSM-5 molecular sieve catalyst modified with La, P, B, Cu, Zn, Mg and Ti. The catalyst was evaluated according to the procedure as described in Example 66. The results are shown in the Table 18 below.

Comparative Example 2

A mordenite having a $SiO_2/Al_2O_3$ molar ratio of 20, manufactured by Shanghai Research Institute of Petrochemical Technology, Sinopec, was modified according to the procedure as described in Example 67, to give a mordenite catalyst modified with Ce, Bi, B, Cu, Li and V. The catalyst was evaluated according to the procedure as described in Example 67. The results are shown in the Table 18 below.

Comparative Example 3

A β zeolite having a $SiO_2/Al_2O_3$ molar ratio of 40, manufactured by Shanghai Research Institute of Petrochemical Technology, Sinopec, was modified according to the procedure as described in Example 66, to give a β zeolite catalyst modified with La, P, Bi, B, Cu, Zn, Ag, Mg, K, Ti and V. The catalyst was evaluated according to the procedure as described in Example 66. The results are shown in the Table 18 below.

Comparative Example 4

A Y zeolite having a $SiO_2/Al_2O_3$ molar ratio of 20, manufactured by Shanghai Research Institute of Petrochemical Technology, Sinopec, was modified according to the procedure as described in Example 67, to give a Y zeolite catalyst modified with La, Ce, P, B, Cu, Zn, Mg, K, Ti and V. The catalyst was evaluated according to the procedure as described in Example 67. The results are shown in the Table 18 below.

TABLE 18

| Comp. Ex. | Molecular sieve | Type and content of modifying elements (wt %) | Ethylene yield (wt %) | Propylene yield (wt %) | Yield of Ethylene plus propylene (wt %) |
|---|---|---|---|---|---|
| Comp. Ex. 1 | ZSM-5 | 2% La + 1% P + 1% B + 1% Cu + 1% Zn + 1% Mg + 1% Ti | 23.33 | 24.64 | 47.97 |
| Comp. Ex. 2 | Mordenite | 2% Ce + 1% Bi + 1% B + 1% Cu + 1% Li + 1% V | 22.84 | 22.72 | 45.56 |
| Comp. Ex. 3 | β zeolite | 2% La + 1% P + 1% Bi + 1% B + 1% Cu + 1% Zn + 1% Ag + 1% Mg + 1% K + 1% Ti + 1% V | 22.25 | 22.67 | 44.92 |
| Comp. Ex. 4 | Y zeolite | 2% La + 2% Ce + 1% P + 1% B + 1% Cu + 1% Zn + 1% Mg + 1% K + 1% Ti + 1% V | 21.54 | 22.60 | 44.14 |

What is claimed is:

1. A process for the production of olefins via catalytic cracking, comprising
   i) converting a cracking feedstock to an effluent comprising ethylene and propylene in the presence of a catalyst composition; and
   ii) isolating ethylene and propylene from the effluent obtained from i),
   wherein the catalyst composition comprises, on weight basis relative to the total weight of the catalyst composition, the following components:
   a) 30 to 99.5% of at least one intergrowth molecular sieve chosen from intergrowth molecular sieves of at least two of ZSM-5, mordenite, β zeolite, Y zeolite, MCM-22, analcite, MCM-49, MCM-48, MCM-56, ZSM-23, and Magadiite molecular sieve;
   b) 0 to 20% of at least one rare earth element or oxides thereof;
   c) 0 to 10% of at least one element from Group VA of the Periodic Table or oxides thereof;
   d) 0 to 10% of at least one element from Group IIIA of the Periodic Table or oxides thereof;
   e) 0 to 20% of at least one element from Group IB or IIB of the Periodic Table or oxides thereof;
   f) 0 to 20% of at least one element from Group IA or IIA of the Periodic Table or oxides thereof; and
   g) 0 to 65% of at least one binder,
   wherein the components b), c), d), e) and f) are supported on the component a), and contents of at least two of the components b), c), d), e) and f) are larger than zero,
   and further wherein the at least one intergrowth molecular sieve is prepared by mixing a silicon source, an aluminum source, an optional templating agent and water, and allowing the mixture to crystallize under hydrothermal conditions and, optionally, in the presence of suitable crystal seeds.

2. The process according to claim 1, wherein the cracking feedstock is naphtha.

3. The process according to claim 1, wherein the process is performed at a reaction temperature ranging from 550 to 750° C.

4. The process according to claim 1, wherein the process is performed at a reaction pressure ranging from 0.001 MPa to 0.5 MPa.

5. The process according to claim 1, wherein the process is performed at a weight hourly space velocity of the cracking feedstock ranging from 0.1 to 10 $h^{-1}$.

6. The process according to claim 1, wherein the process is performed at a weight ratio of water to the cracking feedstock ranging from 0.1:1 to 4:1.

7. The process according to claim 1, wherein the at least one intergrowth molecular sieve is chosen from intergrowth molecular sieves of ZSM-5 and mordenite; intergrowth molecular sieves of ZSM-5 and β zeolite; intergrowth molecular sieves of ZSM-5 and Y zeolite; intergrowth molecular sieves of ZSM-5 and MCM-22; intergrowth molecular sieves of ZSM-5 and MCM-48; intergrowth molecular sieves of ZSM-5 and MCM-49; intergrowth molecular sieves of ZSM-5 and MCM-56; intergrowth molecular sieves of ZSM-5 and ZSM-23; intergrowth molecular sieves of ZSM-5, Magadiite and β zeolite; intergrowth molecular sieves of ZSM-5, mordenite and β zeolite; intergrowth molecular sieves of ZSM-5, mordenite and Y zeolite; intergrowth molecular sieves of ZSM-5, mordenite and MCM-22; intergrowth molecular sieves of ZSM-5, β zeolite and MCM-22; intergrowth molecular sieves of ZSM-5, β zeolite and MCM-49; intergrowth molecular sieves of ZSM-5, β zeolite and MCM-22; intergrowth molecular sieves of ZSM-5, β zeolite and MCM-49; intergrowth molecular sieves of ZSM-5, ZSM-23 and MCM-49; and intergrowth molecular sieves of ZSM-5, ZSM-23 and MCM 22.

8. The process according to claim 1, wherein the at least one intergrowth molecular sieve has a molar ratio of $SiO_2/Al_2O_3$ of from 10 to 1000.

9. The process according to claim 1, wherein the at least one intergrowth molecular sieve comprises 50 to 99wt % of ZSM-5 molecular sieve, and has a molar ratio of $SiO_2/Al_2O_3$ of from 12 to 300.

10. The process according to claim 1, wherein, on weight basis, the content of the at least one intergrowth molecular sieve ranges from 40 to 99%.

11. The process according to claim 1, wherein the at least one rare earth element is chosen from La, Ce, Nd and Pr; the at least one element from Group VA is chosen from P, As, Sb and Bi; the at least one element from Group IIIA is chosen from B, Ga, In and Tl; the at least one element from Group IB or IIB is chosen from Cu, Ag, Au, Zn and Cd; and the at least one element from Group IA or IIA is chosen from Li, K, Rb, Cs, Be, Mg, Ca, Sr and Ba.

12. The process according to claim 1, wherein on weight basis, the content of the at least one rare earth element or oxides thereof ranges from 0.1 to 20%; the content of the at least one element from Group VA or oxides thereof ranges from 0.1 to 10%; the content of the at least one element from Group IIIA or oxides thereof ranges from 0.01 to 10%; the content of the at least one element from Group IB or IIB or oxides thereof ranges from 0.1 to 20%; and the content of the at least one element from Group IA or IIA or oxides thereof ranges from 0.1 to 20%.

13. The process according to claim 1, wherein on weight basis, the content of the at least one rare earth element or oxides thereof ranges from 0.5 to 15%; the content of the at least one element from Group VA or oxides thereof ranges from 0.5 to 5%; the content of the at least one element from Group IIIA or oxides thereof ranges from 0.1 to 5%; the content of the at least one element from Group IB or IIB or oxides thereof ranges from 0.5 to 15%; and the content of the at least one element from Group IA or IIA or oxides thereof ranges from 0.5 to 10%.

14. The process according to claim 1, wherein the catalyst composition further comprises at least one element from Group IVB or VB of the Periodic Table or oxides thereof in an amount of from 0.01 to 2wt %.

15. The process according to claim 14, wherein the at least one element from Group IVB or VB of the Periodic Table is chosen from Ti, Zr, Hf, V, Nb and Ta.

16. The process according to claim 1, wherein the at least one binder is chosen from silica, alumina, and kaolin.

* * * * *